(12) United States Patent
Lee et al.

(10) Patent No.: US 9,512,220 B2
(45) Date of Patent: Dec. 6, 2016

(54) ANTIBODIES AGAINST ANGIOPOIETINS 1 AND 2, AND THEIR USE

(75) Inventors: Eunkyung Lee, Gyeonggi-do (KR); Hyunjung Kang, Jeonlabuk-do (KR); Minhee Kim, Gyeonggi-do (KR); Eun hye Park, Gyeong-sangbuk-do (KR)

(73) Assignee: NEOPHARM CO., LTD., Daejeon (KR)

( * ) Notice: Subject to any disclaimer, the term of this patent is extended or adjusted under 35 U.S.C. 154(b) by 211 days.

(21) Appl. No.: 14/009,048

(22) PCT Filed: Apr. 5, 2011

(86) PCT No.: PCT/KR2011/002338
§ 371 (c)(1),
(2), (4) Date: Sep. 30, 2013

(87) PCT Pub. No.: WO2012/137993
PCT Pub. Date: Oct. 11, 2012

(65) Prior Publication Data
US 2014/0112933 A1    Apr. 24, 2014

(51) Int. Cl.
| C07K 16/00 | (2006.01) |
| C07K 16/28 | (2006.01) |
| C07K 16/26 | (2006.01) |
| C07K 16/22 | (2006.01) |
| A61K 39/00 | (2006.01) |

(52) U.S. Cl.
CPC .............. *C07K 16/26* (2013.01); *C07K 16/22* (2013.01); *A61K 2039/505* (2013.01); *A61K 2039/545* (2013.01); *C07K 2317/76* (2013.01)

(58) Field of Classification Search
None
See application file for complete search history.

(56) References Cited

U.S. PATENT DOCUMENTS

| 7,521,053 | B2 | 4/2009 | Oliner | |
| 7,658,924 | B2 | 2/2010 | Oliner et al. | |
| 2006/0246071 | A1 | 11/2006 | Green et al. | |
| 2009/0123474 | A1* | 5/2009 | Blakey et al. | 424/142.1 |
| 2009/0226447 | A1* | 9/2009 | Boone et al. | 424/139.1 |
| 2010/0159587 | A1 | 6/2010 | Brinkmann et al. | |
| 2011/0027286 | A1 | 2/2011 | Thurston et al. | |
| 2011/0044998 | A1 | 2/2011 | Bedian et al. | |

FOREIGN PATENT DOCUMENTS

WO    2009/105269    8/2009

OTHER PUBLICATIONS

Klimka et al.,Human anti-CD30 recombinant antibodies by guided phage antibody selection using cell panning. British Journal of Cancer (2000) 83:252-260.*
Beiboer et al., Guided selection of a pan carcinoma specific antibody reveals similar binding characteristics yet structural divergence between the original murine antibody and its human equivalent. J. Mol. Biol. 296: 833-849 (2000).*
Brown et al. Tolerance of single, but not multiple, amino acid replacements in antibody VH CDR 2: a means of minimizing B cell wastage from somatic hypermutation? J. Immuno. May 1996, 3285-91.*
Vajdos et al. Comprehensive functional maps of the antigen-binding site of an anti-ErbB2 antibody obtained with shotgun scanning mutagenesis. J. Mol. Biol., Jul. 5, 2002, 320(2):415-28.*
Rudikoff et al Single amino acid substitution altering antigen-binding specificity. Proc Natl Acad Sci U S A. Mar. 1982;79(6):1979-83.*
MacCallum et al. Antibody-antigen Interactions: Contact Analysis and Binding Site Topography. J. Mol. Biol., 262, 732-745, 1996.*
Casset et al . A peptide mimetic of an anti-CD4 monoclonal antibody by rational design. Biochemical and Biophysical Research Communications, 307:198-205, 2003.*
Paul, Fundamental Immunology, 3rd Edition, 1993, pp. 292-295.*
Almagro et al. Humanization of antibodies, Frontiers in Bioscience (2008) 13:1619-1633.*
Krause et al. An insertion mutation that distorts antibody binding site architecture enhances function of a human antibody. MBio. Feb. 8, 2011;2(1):e00345-10.*
Casanovas et al. "Drug Resistance by Evasion of Antiangiogenic Targeting of VEGF Signaling in Late-Stage Pancreatic Islet Tumors". 2005. *Cancer Cell*. vol. 8: 299-309.
Ebos et al. "Accelerated Metastasis After Short-Term Treatment with a Potent Inhibitor of Tumor Angiogenesis". 2009. *Cancer Cell*. vol. 15: 232-239.
Holash et al. "Vessel Cooption, Regression, and Growth in Tumors Mediated by Angiopoietins and VEGF". 1999. *Science*. vol. 284: 1994-1998.
Holliger et al. "Engineered Antibody Fragments and the Rise if Single Domains". 2005. *Nature Biotechnology*. vol. 23(9): 1126-1136.
Huang et al. "Antigiopoitin-1/ Tie-2 Activation Contributes to Vascular Survival and Tumor Growth During VEGF Blockade". 2009. *Int. J. Oncol*. vol. 34(1): 79-87.
Kim et al. "Angiopoietin-2 at High Concentration Can Enhance Endothelial Cell Survival Through the Phosphatidylinositol 3'-kinase/ Akt Signal Transduction Pathway". 2000. *Oncogene*. vol. 19: 4549-4552.
Pàez-Ribes et al. "Antiangiogenic Therapy Elicits Malignant Progression of Tumors to Increased Local Invasion and Distant Metastasis". 2009. *Cancer Cell*. vol. 15: 220-231.
Park et al. "Serum Angiopoietin-2 as a Clinical Marker for Lung Cancer". 2007. *CHEST*. vol. 132: 200-206.
Schliemann et al. "Circulating Angiopoitin-2 is a Strong Prognostic Factor in Acute Myeloid Leukemia". 2007. *Leukemia*. vol. 21: 1901-1906.

(Continued)

*Primary Examiner* — Maher Haddad
(74) *Attorney, Agent, or Firm* — Riverside Law LLP

(57) ABSTRACT

The present invention relates to antibodies against angiopoietins 1 and 2, and derivatives of these antibodies. More specifically, the present invention relates to therapeutic use of the antibodies and fragment thereof which specifically bind to angiopoietins 1 and 2.

12 Claims, 2 Drawing Sheets

(56) References Cited

OTHER PUBLICATIONS

Scholz et al. "Angiopoietin-2 Serum Levels are Elevated in Patients with Liver Cirrhosis and Hepatocellular Carcinoma". 2007. *Am. J. Gastroenterol.* vol. 102: 2471-2481.
Stratmann et al. "Cell Type-Specific Expression of Angiopoietin-1 and Angiopoietin-2 Suggests a Role in Glioblastoma Angiogenesis". 1998. *American Journal of Pathology.* vol. 153(5): 1459-1466.
Suri et al. "Requisite Role of Angiopoietin-1 a Ligand for the TIE2 Receptor, during Embryonic Angiogenesis". 1996. *Cell.* vol. 87: 1171-1180.
Suri et al. "Increased Vascularization in Mice Overexpressing Angiopoietin-1". 1998. *Science.* vol. 282:468-471.
Thurston et al. "Leakage-Resistant Blood Vessels in Mice Transgenically Overexpressing Angiopoietin-1". 1999. *Science.* vol. 286: 2511-2514.
Yang et al. "Construction of a Large Synthetic Human scFv Library with Six Diversified CDRs and High Functional Diversity". 2009. *Mol. Cells.* vol. 27: 225-235.
Zagzag et al. "In Situ Expression of Angiopoietins in Astrocytomas Identifies Angiopoietin-2 as an Early Marker of Tumor Angiogenesis". 1999. *Experimental Neurology.* vol. 159: 391-400.
International Search Report issued for International Application No. PCT/KR2011/002338, dated Jan. 19, 2012.

\* cited by examiner

SEQUENCE LISTING

<160> NUMBER OF SEQ ID NOS: 94

<210> SEQ ID NO 1
<211> LENGTH: 363
<212> TYPE: DNA
<213> ORGANISM: Artificial Sequence
<220> FEATURE:
<223> OTHER INFORMATION: Nucleotide sequence of heavy chain variable
      region HC1

<400> SEQUENCE: 1
gaggtgcagc tgttggagtc tgggggaggc ttggtacagc ctgggggtc cctgagactc      60 tcctgtgcag cctctggatt cacctttagc gattattcta tgagctgggt ccgccaggct     120
ccagggaagg ggctggagtg ggtctcagcg atctatcata gtggtagtaa tacatattac     180
gctgattctg taaaaggtcg gttcaccatc tccagagaca attccaagaa cacgctgtat     240
ctgcaaatga acagcctgag agccgaggac acggccgtgt attactgtgc gagagatgtt     300
gaggctagga tgctgcctgc gttcgactac tggggccagg tccactggt caccgtctct      360 agt                                                                   363

<210> SEQ ID NO 2
<211> LENGTH: 121
<212> TYPE: PRT
<213> ORGANISM: Artificial Sequence
<220> FEATURE:
<223> OTHER INFORMATION: Amino acid sequence of heavy chain
      variable region HC1

<400> SEQUENCE: 2

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Ser Met Ser Trp Val Arg Gln Ala Pro Gly Lys Gly Leu Glu Trp Val
            35                  40                  45

Ser Ala Ile Tyr His Ser Gly Ser Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Val Glu Ala Arg Met Leu Pro Ala Phe Asp Tyr Trp Gly
            100                 105                 110

Gln Gly Thr Leu Val Thr Val Ser Ser
            115                 120

<210> SEQ ID NO 3
<211> LENGTH: 381
<212> TYPE: DNA
<213> ORGANISM: Artificial Sequence
<220> FEATURE:
<223> OTHER INFORMATION: Nucleotide sequence of heavy chain variable
      region HC2

<400> SEQUENCE: 3
gaggtgcagc tgttggagtc cggggggaggc ttggtacagc ctgggggggtc cctgagactc      60 tcctgtgcag cctctggatt caccttagc aattatgcta tgagctgggt ccgccaggct     120
ccagggaagg gctggagtg gtctcagtg atctctcctg gtagtggtaa tacatattac     180
gctgattctg taaaaggtcg gttcaccatc tccagagaca attccaagaa cacgctgtat     240
ctgcaaatga acagcctgag agccgaggac acggccgtgt attactgtgc gaaaggtgct     300
cttaagtgta ggcatcggtc gtgttcttct tataatgcta tggacgtctg gggccagggt     360
acactggtca ccgtctctag t                                               381

<210> SEQ ID NO 4
<211> LENGTH: 127
<212> TYPE: PRT
<213> ORGANISM: Artificial Sequence
<220> FEATURE:
<223> OTHER INFORMATION: Amino acid sequence of heavy chain
      variable region HC2

<400> SEQUENCE: 4

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Gly Leu Glu Trp Val
            35                  40                  45

Ser Val Ile Ser Pro Gly Ser Gly Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

```
Ala Lys Gly Ala Leu Lys Cys Arg His Arg Ser Cys Ser Ser Tyr Asn
            100                 105                 110

Ala Met Asp Val Trp Gly Gln Gly Thr Leu Val Thr Val Ser Ser
            115                 120                 125

<210> SEQ ID NO 5
<211> LENGTH: 366
<212> TYPE: DNA
<213> ORGANISM: Artificial Sequence
<220> FEATURE:
<223> OTHER INFORMATION: Nucleotide sequence of heavy chain variable
      region HC3

<400> SEQUENCE: 5
gaggtgcagc tgttggagtc tgggggaggc ttggtacagc ctggggggtc cctgagactc      60
tcctgtgcag cctctggatt cacctttagc gattattata tgagctgggt ccgccaggct     120
ccagggaagg ggctggagtg ggtctcatcg atctcttatg atgatggtag tcgtaaatat     180
tacgctgatt ctggtaaaag gtcggttacc atctccagag acaattccaa gaacacgctg     240
tatctgcaaa tgaacagcct gagagccgag gacacggccg tgtattactg tgcgagagat     300
cgttctactt tgcgtcttga tagtttcgac tactggggcc agggtacact ggtcaccgtc     360
tctagt                                                                366

<210> SEQ ID NO 6
<211> LENGTH: 122
<212> TYPE: PRT
<213> ORGANISM: Artificial Sequence
<220> FEATURE:
<223> OTHER INFORMATION: Amino acid sequence of heavy chain
      variable region HC3

<400> SEQUENCE: 6

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Val Arg Gln Ala Pro Gly Lys Gly Leu Glu Trp Val
        35                  40                  45

Ser Ser Ile Ser Tyr Asp Asp Gly Ser Arg Lys Tyr Tyr Ala Asp Ser
    50                  55                  60

Gly Lys Arg Ser Val Thr Ile Ser Arg Asp Asn Ser Lys Asn Thr Leu
65                  70                  75                  80

Tyr Leu Gln Met Asn Ser Leu Arg Ala Glu Thr Ala Val Tyr Tyr
            85                  90                  95

Cys Ala Arg Asp Arg Ser Thr Leu Arg Leu Asp Ser Phe Asp Tyr Trp
            100                 105                 110

Gly Gln Gly Thr Leu Val Thr Val Ser Ser
            115                 120

<210> SEQ ID NO 7
<211> LENGTH: 363
<212> TYPE: DNA
<213> ORGANISM: Artificial Sequence
<220> FEATURE:
<223> OTHER INFORMATION: Nucleotide sequence of heavy chain variable
      region HC4

<400> SEQUENCE: 7
gaggtgcagc tgttggagtc cggggggaggc ctggtacagc ctggggggtc cctgagactc     60
```

```
tcctgtgcag cctctggatt cacctttagc aattatgcta tgagctgggt ccgccaggct        120
ccagggaagg ggctggagtg ggtctcagcg atctctcatg gtggtagtag taaatattac        180
gctgattctg taaaaggtcg gttcaccatc tccagagaca attccaagaa cacgctgtat        240
ctgcaaatga acagcctgag agccgaggac acggccgtgt attactgtgc gagagatcgt        300
actgcgtcgc ttttggatgg tttcgactac tggggccagg gtacactggt caccgtctct        360
agt                                                                     363
```

<210> SEQ ID NO 8
<211> LENGTH: 121
<212> TYPE: PRT
<213> ORGANISM: Artificial Sequence
<220> FEATURE:
<223> OTHER INFORMATION: Amino acid sequence of heavy chain
      variable region HC4

<400> SEQUENCE: 8

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Gly Leu Glu Trp Val
        35                  40                  45

Ser Ala Ile Ser His Gly Gly Ser Ser Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Thr Ala Ser Leu Leu Asp Gly Phe Asp Tyr Trp Gly
            100                 105                 110

Gln Gly Thr Leu Val Thr Val Ser Ser
        115                 120
```

<210> SEQ ID NO 9
<211> LENGTH: 381
<212> TYPE: DNA
<213> ORGANISM: Artificial Sequence
<220> FEATURE:
<223> OTHER INFORMATION: Nucleotide sequence of heavy chain variable
      region HC5

<400> SEQUENCE: 9

```
gaggtgcagc tgttggagtc tgggggaggc ttggtacaga ctgggggtc cctgagactc         60 tcctgtgcag cctctggatt cacctttagc gattatgcta tgagctgggt ccgccaggct       120
ccagggaagg ggctggagtg ggtctcatcg atctcttatg atggtagtag taaatattac       180
gctgattctg taaaaggtcg gttcaccatc tccagagaca attccaagaa cacgctgtat       240
ctgcaaatga acagcctgag agccgaggac acggccgtgt attactgtgc gagacttgct       300
ggtgctcgtg aggatcatcc tgcgtcttct gatgatgcta tggacgtctg gggccagggt       360
acactggtca ccgtctctag t                                                 381
```

<210> SEQ ID NO 10
<211> LENGTH: 127
<212> TYPE: PRT
<213> ORGANISM: Artificial Sequence
<220> FEATURE:
<223> OTHER INFORMATION: Amino acid sequence of heavy chain variable region HC5

<400> SEQUENCE: 10

Glu Val Gln Leu Leu Glu Ser Gly Gly Gly Leu Val Gln Thr Gly Gly
1               5                   10                  15

Ser Leu Arg Leu Ser Cys Ala Ala Ser Gly Phe Thr Phe Ser Asp Tyr
            20                  25                  30

Ala Met Ser Trp Val Arg Gln Ala Pro Gly Lys Gly Leu Glu Trp Val
        35                  40                  45

Ser Ser Ile Ser Tyr Asp Gly Ser Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Ala Gly Ala Arg Glu Asp His Pro Ala Ser Ser Asp Asp
            100                 105                 110

Ala Met Asp Val Trp Gly Gln Gly Thr Leu Val Thr Val Ser Ser
        115                 120                 125

<210> SEQ ID NO 11
<211> LENGTH: 381
<212> TYPE: DNA
<213> ORGANISM: Artificial Sequence
<220> FEATURE:
<223> OTHER INFORMATION: Nucleotide sequence of heavy chain variable
      region HC6

<400> SEQUENCE: 11
gaggtgcagc tgttggagtc tgggggaggc ttggtacagc ctggggggtc cctgagactc      60
tcctgtgcag cctctggatt cacctttagc aattattcta tgagctgggt ccgccaggct     120
ccagggaagg gctggagtg gtctcaggg atctcttctg atggtggtag tacatattac      180
gctgattctg taagaggtcg gttcaccatc tccagagaca attccaagaa cacgctgtat     240
ctgcaaatga acagcctggg agccgaggac acggccgtgt attactgtgc gagagatgct     300
cttcagcctc ggaataagat gtggtattat tattatggta tggacgtctg gggccagggt     360
acactggtca ccgtctctag t                                                381

<210> SEQ ID NO 12
<211> LENGTH: 127
<212> TYPE: PRT
<213> ORGANISM: Artificial Sequence
<220> FEATURE:
<223> OTHER INFORMATION: Amino acid sequence of heavy chain
      variable region HC6

<400> SEQUENCE: 12

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ser Met Ser Trp Val Arg Gln Ala Pro Gly Lys Gly Leu Glu Trp Val
        35                  40                  45

Ser Gly Ile Ser Ser Asp Gly Gly Ser Thr Tyr Tyr Ala Asp Ser Val
    50                  55                  60

Arg Gly Arg Phe Thr Ile Ser Arg Asp Asn Ser Lys Asn Thr Leu Tyr
65                  70                  75                  80

```
Leu Gln Met Asn Ser Leu Gly Ala Glu Asp Thr Ala Val Tyr Tyr Cys
                85                  90                  95

Ala Arg Asp Ala Leu Gln Pro Arg Asn Lys Met Trp Tyr Tyr Tyr
        100                 105                 110

Gly Met Asp Val Trp Gly Gln Gly Thr Leu Val Thr Val Ser Ser
        115                 120                 125

<210> SEQ ID NO 13
<211> LENGTH: 381
<212> TYPE: DNA
<213> ORGANISM: Artificial Sequence
<220> FEATURE:
<223> OTHER INFORMATION: Nucleotide sequence of heavy chain variable
      region HC7

<400> SEQUENCE: 13
gaggtgcagc tgttggagtc tgggggaggc ttggtacagc ctgggggtc cctgagactc      60 tcctgtgcag cctctggatt cacctttagc gatcatgcta tgagctgggt ccgccaggct    120
ccagggaagg ggctggagtg ggtctcagcg atctcttctg gtggtagtag tacatattac    180
gctgattctg taagaggtcg gttcaccatc tccagagaca attccaagaa cacgctgtat    240
ctgcaaatga acagcctggg agccgaggac acggccgtgt attactgtgc gaaatctggt    300
attacgaagg tgaggaagac gatgtcttct gcttatggta tggacgtctg gggccagggt    360
acactggtca ccgtctctag t                                              381

<210> SEQ ID NO 14
<211> LENGTH: 127
<212> TYPE: PRT
<213> ORGANISM: Artificial Sequence
<220> FEATURE:
<223> OTHER INFORMATION: Amino acid sequence of heavy chain
      variable region HC7

<400> SEQUENCE: 14

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp His
            20                  25                  30

Ala Met Ser Trp Val Arg Gln Ala Pro Gly Lys Gly Leu Glu Trp Val
        35                  40                  45

Ser Ala Ile Ser Ser Gly Gly Ser Ser Thr Tyr Tyr Ala Asp Ser Val
    50                  55                  60

Arg Gly Arg Phe Thr Ile Ser Arg Asp Asn Ser Lys Asn Thr Leu Tyr
65                  70                  75                  80

Leu Gln Met Asn Ser Leu Gly Ala Glu Asp Thr Ala Val Tyr Tyr Cys
                85                  90                  95

Ala Lys Ser Gly Ile Thr Lys Val Arg Lys Thr Met Ser Ser Ala Tyr
            100                 105                 110

Gly Met Asp Val Trp Gly Gln Gly Thr Leu Val Thr Val Ser Ser
        115                 120                 125

<210> SEQ ID NO 15
<211> LENGTH: 363
<212> TYPE: DNA
<213> ORGANISM: Artificial Sequence
<220> FEATURE:
<223> OTHER INFORMATION: Nucleotide sequence of heavy chain variable
      region HC8

<400> SEQUENCE: 15
```

```
gaggtgcagc tgttggagtc tgggggaggc ttggtacagc ctgggggtc cctgagactc      60 tcctgtgcag cctctggatt cacctttagc aattattcta tgagctgggt ccgccaggct     120
ccagggaagg ggctggagtg ggtctcagcg atctctcctg gtaatggtaa taaatattac    180
gctgattctg taaaaggtcg gttcaccatc tccagagaca attccaagaa cacgctgtat     240
ctgcaaatga acagcctggg agccgaggac acggccgtgt attactgtgc gaaaggtctt     300
agttcgcttc ttctggtggg gttcgactac tggggccagg gtacactggt caccgtctct     360
agt                                                                   363
```

<210> SEQ ID NO 16
<211> LENGTH: 121
<212> TYPE: PRT
<213> ORGANISM: Artificial Sequence
<220> FEATURE:
<223> OTHER INFORMATION: Amino acid sequence of heavy chain
      variable region HC8

<400> SEQUENCE: 16

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ser Met Ser Trp Val Arg Gln Ala Pro Gly Lys Gly Leu Glu Trp Val
        35                  40                  45

Ser Ala Ile Ser Pro Gly Asn Gly Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Leu Ser Ser Leu Leu Leu Val Gly Phe Asp Tyr Trp Gly
            100                 105                 110

Gln Gly Thr Leu Val Thr Val Ser Ser
        115                 120
```

<210> SEQ ID NO 17
<211> LENGTH: 381
<212> TYPE: DNA
<213> ORGANISM: Artificial Sequence
<220> FEATURE:
<223> OTHER INFORMATION: Nucleotide sequence of heavy chain variable
      region HC9

<400> SEQUENCE: 17

```
gaggtgcagc tgttggagtc tgggggaggc ttggtacagc ctgggggtc cctgagactc      60 tcctgtgcag cctctggatt cacctttagc gattattcta tgagctgggt ccgccaggct    120
ccagggaagg ggctggagtg ggtctcagcg atctatccta gtagtaa taaatattac      180 gctgattctg taaaaggtcg gttcaccatc tccagagaca attccaagaa cacgctgtat     240
ctgcaaatga acagcctgag agccgaggac acggccgtgt attactgtgc gagagatact    300
agtcggtgtg ataagactaa gtgttattat tatgatgcta tggacgtctg gggccaggt    360 acactggtca ccgtctctag t                                              381
```

<210> SEQ ID NO 18
<211> LENGTH: 127
<212> TYPE: PRT

<213> ORGANISM: Artificial Sequence
<220> FEATURE:
<223> OTHER INFORMATION: Amino acid sequence of heavy chain
      variable region HC9

<400> SEQUENCE: 18

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Ser Met Ser Trp Val Arg Gln Ala Pro Gly Lys Gly Leu Glu Trp Val
        35                  40                  45

Ser Ala Ile Tyr Pro Ser Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Thr Ser Arg Cys Asp Lys Thr Lys Cys Tyr Tyr Tyr Asp
            100                 105                 110

Ala Met Asp Val Trp Gly Gln Gly Thr Leu Val Thr Val Ser Ser
        115                 120                 125

<210> SEQ ID NO 19
<211> LENGTH: 381
<212> TYPE: DNA
<213> ORGANISM: Artificial Sequence
<220> FEATURE:
<223> OTHER INFORMATION: Nucleotide sequence of heavy chain variable
      region HC10

<400> SEQUENCE: 19
gaggtgcagc tggtggagtc tgggggaggc ttggtacagc ctgggggtc cctgagactc      60 tcctgtgcag cctctggatt caccttagc aattatgcta tgagctgggt ccgccaggct     120
ccagggaagg gctggagtg gtctcatgg atctatcctg ataatggtaa tacatattac     180
gctgattctg taaaggtcg gttcaccatc tccagagaca attccaagaa cacgctgtat    240
ctgcaaatga acagcctgag agccgaggac acggccgtgt attactgtgc gaaatatagt    300
cttgataagt atacgccgtg gccgtattct tattatggta tggacgtctg gggccagggt    360
acactggtca ccgtctctag t                                              381

<210> SEQ ID NO 20
<211> LENGTH: 127
<212> TYPE: PRT
<213> ORGANISM: Artificial Sequence
<220> FEATURE:
<223> OTHER INFORMATION: Amino acid sequence of heavy chain
      variable region HC10

<400> SEQUENCE: 20

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Gly Leu Glu Trp Val
        35                  40                  45

Ser Trp Ile Tyr Pro Asp Asn Gly Asn Thr Tyr Tyr Ala Asp Ser Val
    50                  55                  60

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Tyr Ser Leu Asp Lys Tyr Thr Pro Trp Pro Tyr Ser Tyr Tyr
            100                 105                 110

Gly Met Asp Val Trp Gly Gln Gly Thr Leu Val Thr Val Ser Ser
        115                 120                 125

<210> SEQ ID NO 21
<211> LENGTH: 363
<212> TYPE: DNA
<213> ORGANISM: Artificial Sequence
<220> FEATURE:
<223> OTHER INFORMATION: Nucleotide sequence of heavy chain variable
      region HC11

<400> SEQUENCE: 21
gaggtgcagc tgttggagtc tgggggaggc ttggtacagc ctgggggtc cctgagactc       60 tcctgtgcag cctctggatt caccttagc gattatgcta tgagctgggt ccgccaggct     120
ccagggaagg ggctggagtg ggtctcagcg atctcttctg atggtggtag tacatattac     180
gctgattctg tacaaggtcg gttcaccatc tccagagaca attccaagaa cacgctgtat     240
ctgcaaatga acagcctgag agccgaggac acggccgtgt attactgtgc gagagatcgt     300
tcgaagttga tgttgcctgg tttcgactac tggggccagg gtacactggt caccgtctct     360
agt                                                                   363

<210> SEQ ID NO 22
<211> LENGTH: 121
<212> TYPE: PRT
<213> ORGANISM: Artificial Sequence
<220> FEATURE:
<223> OTHER INFORMATION: Amino acid sequence of heavy chain
      variable region HC11

<400> SEQUENCE: 22

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Asp Tyr
             20                  25                  30

Ala Met Ser Trp Val Arg Gln Ala Pro Gly Lys Gly Leu Glu Trp Val
         35                  40                  45

Ser Ala Ile Ser Ser Asp Gly Gly Ser Thr Tyr Tyr Ala Asp Ser Val
 50                  55                  60

Gln Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asp Arg Ser Lys Leu Met Leu Pro Gly Phe Asp Tyr Trp Gly
            100                 105                 110

Gln Gly Thr Leu Val Thr Val Ser Ser
        115                 120

<210> SEQ ID NO 23
<211> LENGTH: 381
<212> TYPE: DNA
<213> ORGANISM: Artificial Sequence
<220> FEATURE:
<223> OTHER INFORMATION: Nucleotide sequence of heavy chain variable
```

-continued region HC12

<400> SEQUENCE: 23

```
gaggtgcagc tgttggagtc cgggggaggc ttggtacagc ctgggggggtc cctgagactc      60
tcctgtgcag cctctggatt cacctttagc aattatgcta tgagctgggt ccgccaggct     120
ccagggaagg ggctggagtg ggtctcagtg atctctcctg gtagtggtaa tacatattac     180
gctgattctg taaaaggtcg gttcaccatc tccagagaca attccaagaa cacgctgtat     240
ctgcaaatga acagcctgag agccgaggac acggccgtgt attactgtgc gaaaggtgct     300
cttaagtgta ggcatcggtc gtgttcttct tataatgcta tggacgtctg ggcccagggt     360
acactggtca ccgtctctag t                                                381
```

<210> SEQ ID NO 24
<211> LENGTH: 127
<212> TYPE: PRT
<213> ORGANISM: Artificial Sequence
<220> FEATURE:
<223> OTHER INFORMATION: Amino acid sequence of heavy chain
      variable region HC12

<400> SEQUENCE: 24

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Gly Leu Glu Trp Val
        35                  40                  45

Ser Val Ile Ser Pro Gly Ser Gly Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Ala Leu Lys Cys Arg His Arg Ser Cys Ser Ser Tyr Asn
            100                 105                 110

Ala Met Asp Val Trp Gly Gln Gly Thr Leu Val Thr Val Ser Ser
        115                 120                 125
```

<210> SEQ ID NO 25
<211> LENGTH: 348
<212> TYPE: DNA
<213> ORGANISM: Artificial Sequence
<220> FEATURE:
<223> OTHER INFORMATION: Nucleotide sequence of heavy chain variable
      region HC13

<400> SEQUENCE: 25

```
gaggtgcagc tgttggagtc tgggggaggc ttggtacagc ctgggggggtc cctgagactc      60
tcctgtgcag cctctggatt cacctttagc agttatgata tgagctgggt ccgccaggct     120
ccagggaagg ggctggagtg ggtctcatgg atccctcctg atagtggtag tatatattac     180
gctgattctg taaaaggtcg gttcaccatc tccagagaca attccaagaa cacgctgtat     240
ctgcaaatga acagcctgag agccgaggac acggccgtgt attactgtgc gagacatgct     300
ccggttttcg actactgggg ccagggtaca ctggtcaccg tctctagt                  348
```

<210> SEQ ID NO 26
<211> LENGTH: 116

```
<212> TYPE: PRT
<213> ORGANISM: Artificial Sequence
<220> FEATURE:
<223> OTHER INFORMATION: Amino acid sequence of heavy chain
      variable region HC13

<400> SEQUENCE: 26

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Trp Ile Pro Pro Asp Ser Gly Ser Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg His Ala Pro Val Phe Asp Tyr Trp Gly Gln Gly Thr Leu Val
            100                 105                 110

Thr Val Ser Ser
            115

<210> SEQ ID NO 27
<211> LENGTH: 348
<212> TYPE: DNA
<213> ORGANISM: Artificial Sequence
<220> FEATURE:
<223> OTHER INFORMATION: Nucleotide sequence of heavy chain variable
      region HC14

<400> SEQUENCE: 27
gaggtgcagc tgttggagtc tgggggaggc ttggtacagc ctgggggggtc cctgggactc      60 tcctgtgcag cctctggatt caccctttagc aattatgata tgagctgggt ccgccaggct     120
ccagggaagg gctggagtg gtctcatgg atctctcctg atagtagtag tacatattac        180
gctgattctg taaaaggtcg gttcaccatc tccagagaca attccaagaa cacgctgtat      240
ctgcaaatga acagcctgag agccgaggac acggccgtgt attactgtgc gagatctgtt      300
atgcctttcg actactgggg ccagggtaca ctggtcaccg tctctagt                   348

<210> SEQ ID NO 28
<211> LENGTH: 116
<212> TYPE: PRT
<213> ORGANISM: Artificial Sequence
<220> FEATURE:
<223> OTHER INFORMATION: Amino acid sequence of heavy chain
      variable region HC14

<400> SEQUENCE: 28

Glu Val Gln Leu Leu Glu Ser Gly Gly Gly Leu Val Gln Pro Gly Gly
1               5                   10                  15

Ser Leu Gly Leu Ser Cys Ala Ala Ser Gly Phe Thr Leu Ser Asn Tyr
            20                  25                  30

Asp Met Ser Trp Val Arg Gln Ala Pro Gly Lys Gly Leu Glu Trp Val
        35                  40                  45

Ser Trp Ile Ser Pro Asp Ser Ser Thr Tyr Tyr Ala Asp Ser Val
    50                  55                  60

Lys Gly Arg Phe Thr Ile Ser Arg Asp Asn Ser Lys Asn Thr Leu Tyr
```

```
                65                   70                  75                  80
Leu Gln Met Asn Ser Leu Arg Ala Glu Asp Thr Ala Val Tyr Tyr Cys
                        85                  90                  95

Ala Arg Ser Val Met Pro Phe Asp Tyr Trp Gly Gln Gly Thr Leu Val
                    100                 105                 110

Thr Val Ser Ser
        115

<210> SEQ ID NO 29
<211> LENGTH: 348
<212> TYPE: DNA
<213> ORGANISM: Artificial Sequence
<220> FEATURE:
<223> OTHER INFORMATION: Nucleotide sequence of heavy chain variable
      region HC15

<400> SEQUENCE: 29
gaggtgcagc tgttggagtc tgggggaggc ttggtacagc ctgggggggtc cctgagactc      60 tcctgtgcag cctctggatt cacctttagc gattatgata tgagctgggt ccgccaggct     120
ccaggggagg ggctggagtg ggtctcatgg atctctcctg atagtggtag tatatattac     180
gctgattctg taaaaggtcg gttcaccatc tccagagaca attccaagaa cacgctgtat     240
ctgcaaatga acagcctgag agccgaggac gcggccgtgt attactgtgc gagacttgct     300
cctgagttcg actactgggg ccagggtaca ctggtcaccg tctctagt                  348

<210> SEQ ID NO 30
<211> LENGTH: 116
<212> TYPE: PRT
<213> ORGANISM: Artificial Sequence
<220> FEATURE:
<223> OTHER INFORMATION: Amino acid sequence of heavy chain
      variable region HC15

<400> SEQUENCE: 30

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Asp Met Ser Trp Val Arg Gln Ala Pro Gly Glu Gly Leu Glu Trp Val
        35                  40                  45

Ser Trp Ile Ser Pro Asp Ser Gly Ser Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Ala Ala Val Tyr Tyr Cys
                85                  90                  95

Ala Arg Leu Ala Pro Glu Phe Asp Tyr Trp Gly Gln Gly Thr Leu Val
            100                 105                 110

Thr Val Ser Ser
        115

<210> SEQ ID NO 31
<211> LENGTH: 366
<212> TYPE: DNA
<213> ORGANISM: Artificial Sequence
<220> FEATURE:
<223> OTHER INFORMATION: Nucleotide sequence of heavy chain variable
      region HC16

<400> SEQUENCE: 31
```

```
gaggtgcagc tgttggagtc tgggggaggc ttggtacagc ctgggggtc cctgagactc    60 tcctgtgcag cctctggatt cacctttagc gattattata tgagctgggt ccgccaggct   120
ccagggaagg ggctggagtg ggtctcatcg atctcttatg atgatggtag tcgtaaatat   180
tacgctgatt ctgtaaaaag gtcggttacc atctccagag acaattccaa gaacacgctg   240
tatctgcaaa tgaacagcct gagagccgag gacacggccg tgtattactg tgcgagagat   300
cgttctactt tgcgtcttga tagtttcgac tactggggcc agggtacact ggtcaccgtc   360
tctagt                                                              366
```

<210> SEQ ID NO 32
<211> LENGTH: 122
<212> TYPE: PRT
<213> ORGANISM: Artificial Sequence
<220> FEATURE:
<223> OTHER INFORMATION: Amino acid sequence of heavy chain
      variable region HC16

<400> SEQUENCE: 32

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Val Arg Gln Ala Pro Gly Lys Gly Leu Glu Trp Val
        35                  40                  45

Ser Ser Ile Ser Tyr Asp Asp Gly Ser Arg Lys Tyr Tyr Ala Asp Ser
    50                  55                  60

Gly Lys Arg Ser Val Thr Ile Ser Arg Asp Asn Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Arg Asp Arg Ser Thr Leu Arg Leu Asp Ser Phe Asp Tyr Trp
            100                 105                 110

Gly Gln Gly Thr Leu Val Thr Val Ser Ser
        115                 120
```

<210> SEQ ID NO 33
<211> LENGTH: 381
<212> TYPE: DNA
<213> ORGANISM: Artificial Sequence
<220> FEATURE:
<223> OTHER INFORMATION: Nucleotide sequence of heavy chain variable
      region HC17

<400> SEQUENCE: 33

```
gaggtgcagc tgttggagtc tgggggaggc ttggtacagc ctgggggtc cctgagactc    60 tcctgtgcag cctctggatt cacctttagc agttattcta tgagctgggt ccgccaggct   120
ccagggaagg ggctggagtg ggtctcagcg atctctcctg gtagtagtaa taaatattac   180
gctgattctg taaaaggtcg gttcaccatc tccagagaca attccaagaa cacgctgtat   240
ctgcaaatga acagcctgag agccgaggac acggccgtgt attactgtgc gagaggtgtt   300
agtcgttcgc ggcattatcc tacgtattat tataatggta tggacgtctg gggccaggt   360 acactggtca ccgtctctag t                                             381
```

<210> SEQ ID NO 34
<211> LENGTH: 127
<212> TYPE: PRT

<213> ORGANISM: Artificial Sequence
<220> FEATURE:
<223> OTHER INFORMATION: Amino acid sequence of heavy chain
      variable region HC17

<400> SEQUENCE: 34

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ser Met Ser Trp Val Arg Gln Ala Pro Gly Lys Gly Leu Glu Trp Val
        35                  40                  45

Ser Ala Ile Ser Pro Gly Ser Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Val Ser Arg Ser Arg His Tyr Pro Thr Tyr Tyr Tyr Asn
            100                 105                 110

Gly Met Asp Val Trp Gly Gln Gly Thr Leu Val Thr Val Ser Ser
        115                 120                 125
```

<210> SEQ ID NO 35
<211> LENGTH: 348
<212> TYPE: DNA
<213> ORGANISM: Artificial Sequence
<220> FEATURE:
<223> OTHER INFORMATION: Nucleotide sequence of heavy chain variable
      region HC18

<400> SEQUENCE: 35

```
gaggtgcagc tgttggagtc tgggggaggc ttggtacagc ctggggggtc cctgagactc    60
tcctgtgcag cctctggatt cacctttagc gattatgata tgagctgggt ccgccaggct   120
ccagggaagg gctggagtg gtctcatgg atctctcctg atgatggtag tatatattac    180
gctgattctg taaaaggtcg gttcaccatc tccagagaca attccaagaa cacgctgtat   240
ctgcaaatga acagcctgag agccgaggac acggccgtgt attactgtgc gagatctgtg   300
ctgccgttcg actactgggg ccagggtaca ctggtcaccg tctctagt               348
```

<210> SEQ ID NO 36
<211> LENGTH: 116
<212> TYPE: PRT
<213> ORGANISM: Artificial Sequence
<220> FEATURE:
<223> OTHER INFORMATION: Amino acid sequence of heavy chain
      variable region HC18

<400> SEQUENCE: 36

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Asp Met Ser Trp Val Arg Gln Ala Pro Gly Lys Gly Leu Glu Trp Val
        35                  40                  45

Ser Trp Ile Ser Pro Asp Asp Gly Ser Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80
```

Leu Gln Met Asn Ser Leu Arg Ala Glu Asp Thr Ala Val Tyr Tyr Cys
            85                  90                  95

Ala Arg Ser Val Leu Pro Phe Asp Tyr Trp Gly Gln Gly Thr Leu Val
            100                 105                 110

Thr Val Ser Ser
        115

<210> SEQ ID NO 37
<211> LENGTH: 372
<212> TYPE: DNA
<213> ORGANISM: Artificial Sequence
<220> FEATURE:
<223> OTHER INFORMATION: Nucleotide of heavy chain variable region HC19

<400> SEQUENCE: 37
gaggtgcagc tggtacagtc tgggggaggt gtggtccagc ctggagggtc cctgagactc        60
tcctgtgcag cgtctggatt caccttcagt aaatatggca tgcactgggt ccgccaggct       120
ccaggcaagg ggctggaatg gctggcattt atttggtttg atggaagtaa taaattctat       180
gcagactccg tgaagggccg attcaccgtc tccagagaca attccaagaa caccctgttt       240
ctgcaaatga acagcctgag agccgaggac acggccgtgt attactgtgc gagaggccat       300
aagtttggtg actacgacgg ggtggaccgg ttcgacccct ggggccaggg aaccctggtc       360
accgtctcta gt                                                          372

<210> SEQ ID NO 38
<211> LENGTH: 124
<212> TYPE: PRT
<213> ORGANISM: Artificial Sequence
<220> FEATURE:
<223> OTHER INFORMATION: Amino acid sequence of heavy chain
      variable region HC19

<400> SEQUENCE: 38

Glu Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Lys Tyr
            20                  25                  30

Gly Met His Trp Val Arg Gln Ala Pro Gly Lys Gly Leu Glu Trp Leu
        35                  40                  45

Ala Phe Ile Trp Phe Asp Gly Ser Asn Lys Phe Tyr Ala Asp Ser Val
    50                  55                  60

Lys Gly Arg Phe Thr Val Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
            85                  90                  95

Ala Arg Gly His Lys Phe Gly Asp Tyr Asp Gly Val Asp Arg Phe Asp
            100                 105                 110

Pro Trp Gly Gln Gly Thr Leu Val Thr Val Ser Ser
        115                 120

<210> SEQ ID NO 39
<211> LENGTH: 363
<212> TYPE: DNA
<213> ORGANISM: Artificial Sequence
<220> FEATURE:
<223> OTHER INFORMATION: Nucleotide sequence of heavy chain variable
      region HC20

<400> SEQUENCE: 39

```
gaggtgcagc tggtggagtc tgggggaggc ttggtacagc ctgggggtc cctgagactc      60 tcctgtgcag cctctggatt cacctttagc agctatgcca tgagctgggt ccgccaggct    120
ccagggaagg ggctggagtg ggtctcagct attagtggta gtggtggtag cacattctac    180
gcagactccg tgaagggccg gttcaccatc tccagagaca attccaagaa cacggtgtat    240
ctgcaaatga acagtctgag agccgaggac acggccgtgt attactgtgc gagagggggc    300
gactacggtt cggggactta ttatgacctc tggggccgcg gaaccctgat caccgtctct    360
agt                                                                  363
```

<210> SEQ ID NO 40
<211> LENGTH: 121
<212> TYPE: PRT
<213> ORGANISM: Artificial Sequence
<220> FEATURE:
<223> OTHER INFORMATION: Amino acid sequence of heavy chain
      variable region HC20

<400> SEQUENCE: 40

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Phe Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Ala Glu Asp Thr Ala Val Tyr Tyr Cys
                85                  90                  95

Ala Arg Gly Gly Asp Tyr Gly Ser Gly Thr Tyr Tyr Asp Leu Trp Gly
            100                 105                 110

Arg Gly Thr Leu Ile Thr Val Ser Ser
        115                 120
```

<210> SEQ ID NO 41
<211> LENGTH: 363
<212> TYPE: DNA
<213> ORGANISM: Artificial Sequence
<220> FEATURE:
<223> OTHER INFORMATION: Nucleotide sequence of heavy chain variable
      region HC21

<400> SEQUENCE: 41

```
gaggtgcagc tggtagagtc gggggggaggc gtggttcagc ctgggggtc cctgagactc     60 tcctgtgtag cctctggatt cacttttaat gaacacgcca tgcactgggt ccgtcaagct   120
ccaggaaagg gtctggagtg gatcgctctt attggtgcgg atggtgtcac tacttactct   180
gcagactctg tgagggccg aatcaccatc tcccgagaca cagcaaaaa ctccctgtat    240 ctgcaaatga acagtctgag agccgaggac acggccgtgt attactgtgc gagagggtct    300
cgctttgata cgagtggtcc cattgatcat tggggccagg gaaccccggt caccgtctct    360
agt                                                                  363
```

<210> SEQ ID NO 42
<211> LENGTH: 121
<212> TYPE: PRT

<213> ORGANISM: Artificial Sequence
<220> FEATURE:
<223> OTHER INFORMATION: Amino acid sequence of heavy chain
    variable region HC21

<400> SEQUENCE: 42

Glu Val Gln Leu Val Glu Ser Gly Gly Val Val Gln Pro Gly Gly
1               5                   10                  15

Ser Leu Arg Leu Ser Cys Val Ala Ser Gly Phe Thr Phe Asn Glu His
            20                  25                  30

Ala Met His Trp Val Arg Gln Ala Pro Gly Lys Gly Leu Glu Trp Ile
        35                  40                  45

Ala Leu Ile Gly Ala Asp Gly Val Thr Thr Tyr Ser Ala Asp Ser Val
    50                  55                  60

Glu Gly Arg Ile Thr Ile Ser Arg Asp Asn Ser Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Ser Arg Phe Asp Thr Ser Gly Pro Ile Asp His Trp Gly
            100                 105                 110

Gln Gly Thr Pro Val Thr Val Ser Ser
        115                 120

<210> SEQ ID NO 43
<211> LENGTH: 351
<212> TYPE: DNA
<213> ORGANISM: Artificial Sequence
<220> FEATURE:
<223> OTHER INFORMATION: Nucleotide sequence of heavy chain variable
    region HC22

<400> SEQUENCE: 43
gaggtgcagc tggtacagtc tggggctgag gtgaagaagc ctggggcctc agtgaaggtt      60
tcctgcaagg cttctggagg cacctttcagc agctatgcta tcagctgggt gcgacaggcc   120
cctggacaag ggcttgagtg gatgggaggg atcatcccta tctttggtac agcaaactac    180
gcacagaagt tccagggcag agtcacgatt accgcggacg aatccacgag cacagcctac    240
atggagctga gcagcctgag atctgaggac acggccgtgt attactgtgc gagaggcggt    300
tcggggaggt ttgactactg gggccaggga accctggtca ccgtctctag t             351

<210> SEQ ID NO 44
<211> LENGTH: 117
<212> TYPE: PRT
<213> ORGANISM: Artificial Sequence
<220> FEATURE:
<223> OTHER INFORMATION: Amino acid sequence of heavy chain
    variable region HC22

<400> SEQUENCE: 44

Glu Val Gln Leu Val Gln Ser Gly Ala Glu Val Lys Lys Pro Gly Ala
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

```
Met Glu Leu Ser Ser Leu Arg Ser Glu Asp Thr Ala Val Tyr Tyr Cys
                85                  90                  95

Ala Arg Gly Gly Ser Gly Arg Phe Asp Tyr Trp Gly Gln Gly Thr Leu
            100                 105                 110

Val Thr Val Ser Ser
        115

<210> SEQ ID NO 45
<211> LENGTH: 330
<212> TYPE: DNA
<213> ORGANISM: Artificial Sequence
<220> FEATURE:
<223> OTHER INFORMATION: Nucleotide sequence of light chain variable
      region LC1

<400> SEQUENCE: 45
cagtctgtgc tgactcagcc accctcagcg tctgggaccc ccgggcagag ggtcaccatc      60
tcttgtagtg gctcttcatc taatattggc aataatgatg tctcctggta ccagcagctc     120
ccaggaacgg cccccaaact cctcatctat tctgatagtc agcggccaag cggggtccct     180
gaccgattct ctggctccaa gtctggcacc tcagcctccc tggccatcag tgggctccgg     240
tccgaggatg aggctgatta ttactgtggt tcttgggatg ctagcctgaa tggttatgtc     300
ttcggcggag gcaccaagct gacggtccta                                      330

<210> SEQ ID NO 46
<211> LENGTH: 110
<212> TYPE: PRT
<213> ORGANISM: Artificial Sequence
<220> FEATURE:
<223> OTHER INFORMATION: Amino acid sequence of light chain
      variable region LC1

<400> SEQUENCE: 46

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Asn Asn
            20                  25                  30

Asp Val Ser Trp Tyr Gln Gln Leu Pro Gly Thr Ala Pro Lys Leu Leu
        35                  40                  45

Ile Tyr Ser Asp Ser Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Ser Trp Asp Ala Ser Leu
                85                  90                  95

Asn Gly Tyr Val Phe Gly Gly Gly Thr Lys Leu Thr Val Leu
            100                 105                 110

<210> SEQ ID NO 47
<211> LENGTH: 330
<212> TYPE: DNA
<213> ORGANISM: Artificial Sequence
<220> FEATURE:
<223> OTHER INFORMATION: Nucleotide sequence of light chain variable
      region LC2

<400> SEQUENCE: 47
cagtctgtgc tgactcagcc accctcagcg tctgggaccc ccgggcagag ggtcaccatc      60
tcttgtactg gctcttcatc taatattggc aataatgatg tctcctggta ccagcagctc     120
```

```
ccaggaacgg cccccaaact cctcatctat gataataatc atcggccaag cggggtccct      180
gaccgattct ctggctccaa gtctggcacc tcagcctccc tggccatcag tgggctccgg      240
tccgaggatg aggctgatta ttactgtggt acttgggatg ctagcctgaa tggttatgtc      300
ttcggcggag gcaccaagct gacggtccta                                        330
```

```
<210> SEQ ID NO 48
<211> LENGTH: 110
<212> TYPE: PRT
<213> ORGANISM: Artificial Sequence
<220> FEATURE:
<223> OTHER INFORMATION: Amino acid sequence of light chain
      variable region LC2

<400> SEQUENCE: 48
```

Gln Ser Val Leu Thr Gln Pro Pro Ser Ala Ser Gly Thr Pro Gly Gln
1               5                   10                  15

Arg Val Thr Ile Ser Cys Thr Gly Ser Ser Asn Ile Gly Asn Asn
            20                  25                  30

Asp Val Ser Trp Tyr Gln Gln Leu Pro Gly Thr Ala Pro Lys Leu Leu
        35                  40                  45

Ile Tyr Asp Asn Asn His Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Thr Trp Asp Ala Ser Leu
                85                  90                  95

Asn Gly Tyr Val Phe Gly Gly Gly Thr Lys Leu Thr Val Leu
            100                 105                 110

```
<210> SEQ ID NO 49
<211> LENGTH: 330
<212> TYPE: DNA
<213> ORGANISM: Artificial Sequence
<220> FEATURE:
<223> OTHER INFORMATION: Nucleotide sequence of light chain variable
      region LC3

<400> SEQUENCE: 49
cagtctgtgc tgactcagcc accctcagcg tctgggaccc ccgggcggag ggtcaccatc      60
tcttgtagtg gctcttcacc taatattggc aataatactg tcaactggta ccagcagctc     120
ccaggaacgg cccccaaact cctcatctat tctgatagtc atcggccaag cggggtccct     180
gaccgattct ctggctccaa gtctggcacc tcagcctccc tggccatcag tgggctccgg     240
tccgaggatg aggctgatta ttactgtggt gcttgggatt atagcctgaa tgcttatgtc     300
ttcggcggag gcaccaagct gacggtccta                                        330
```

```
<210> SEQ ID NO 50
<211> LENGTH: 110
<212> TYPE: PRT
<213> ORGANISM: Artificial Sequence
<220> FEATURE:
<223> OTHER INFORMATION: Amino acid sequence of light chain
      variable region LC3

<400> SEQUENCE: 50
```

Gln Ser Val Leu Thr Gln Pro Pro Ser Ala Ser Gly Thr Pro Gly Arg
1               5                   10                  15

Arg Val Thr Ile Ser Cys Ser Gly Ser Ser Pro Asn Ile Gly Asn Asn

```
                  20                  25                  30

Thr Val Asn Trp Tyr Gln Gln Leu Pro Gly Thr Ala Pro Lys Leu Leu
            35                  40                  45

Ile Tyr Ser Asp Ser His Arg Pro Ser Gly Val Pro Asp Arg Phe Ser
        50                  55                  60

Gly Ser Lys Ser Gly Thr Ser Ala Ser Leu Ala Ile Ser Gly Leu Arg
 65                  70                  75                  80

Ser Glu Asp Glu Ala Asp Tyr Tyr Cys Gly Ala Trp Asp Tyr Ser Leu
                    85                  90                  95

Asn Ala Tyr Val Phe Gly Gly Gly Thr Lys Leu Thr Val Leu
                100                 105                 110

<210> SEQ ID NO 51
<211> LENGTH: 330
<212> TYPE: DNA
<213> ORGANISM: Artificial Sequence
<220> FEATURE:
<223> OTHER INFORMATION: Nucleotide sequence of light chain variable
      region LC4

<400> SEQUENCE: 51
cagtctgtgc tgactcagcc accctcagcg tctgggaccc ccgggcagag ggtcaccatc      60
tcttgtagtg gctcttcatc taatattggc aataattatg tcaactggta ccagcagctc     120
ccaggaacgg cccccaaact cctcatctat gctgatagta atcggccaag cggggtccct     180
gaccgattct ctggctccaa gtctggcacc tcagcctccc tggccatcag tgggctccgg     240
tccgaggatg aggctgatta ttactgtggt acttgggatg ctagcctgag tggttatgtc     300
ttcggcggag gcaccaagct gacggtccta                                      330

<210> SEQ ID NO 52
<211> LENGTH: 110
<212> TYPE: PRT
<213> ORGANISM: Artificial Sequence
<220> FEATURE:
<223> OTHER INFORMATION: Amino acid sequence of light chain
      variable region LC4

<400> SEQUENCE: 52

Gln Ser Val Leu Thr Gln Pro Pro Ser Ala Ser Gly Thr Pro Gly Gln
 1               5                  10                  15

Arg Val Thr Ile Ser Cys Ser Gly Ser Ser Ser Asn Ile Gly Asn Asn
                20                  25                  30

Tyr Val Asn Trp Tyr Gln Gln Leu Pro Gly Thr Ala Pro Lys Leu Leu
            35                  40                  45

Ile Tyr Ala Asp Ser Asn Arg Pro Ser Gly Val Pro Asp Arg Phe Ser
        50                  55                  60

Gly Ser Lys Ser Gly Thr Ser Ala Ser Leu Ala Ile Ser Gly Leu Arg
 65                  70                  75                  80

Ser Glu Asp Glu Ala Asp Tyr Tyr Cys Gly Thr Trp Asp Ala Ser Leu
                    85                  90                  95

Ser Gly Tyr Val Phe Gly Gly Gly Thr Lys Leu Thr Val Leu
                100                 105                 110

<210> SEQ ID NO 53
<211> LENGTH: 324
<212> TYPE: DNA
<213> ORGANISM: Artificial Sequence
<220> FEATURE:
<223> OTHER INFORMATION: Nucleotide sequence of light chain variable
``` region LC5

<400> SEQUENCE: 53

```
cagtctgtgc tgactcagcc accctcagcg tctgggaccc ccgggcagag ggtcaccatc      60
tcttgtagcg gcgatagcat tccttctaaa tatgcgtatt ggtaccagca gctcccagga     120
acggccccca aactcctcat ctattctaat aatcagcggc caagcggggt ccctgaccga     180
ttctctggct ccaagtctgg cacctcagcc tccctggcca tcagtgggct ccggtccgag     240
gatgaggctg attattactg cggttcttgg gattctagcc tgagtgctta tgtcttcggc     300
ggaggcacca agctgacggt ccta                                            324
```

<210> SEQ ID NO 54
<211> LENGTH: 108
<212> TYPE: PRT
<213> ORGANISM: Artificial Sequence
<220> FEATURE:
<223> OTHER INFORMATION: Amino acid sequence of light chain
      variable region LC5

<400> SEQUENCE: 54

```
Gln Ser Val Leu Thr Gln Pro Pro Ser Ala Ser Gly Thr Pro Gly Gln
1               5                   10                  15

Arg Val Thr Ile Ser Cys Ser Gly Asp Ser Ile Pro Ser Lys Tyr Ala
            20                  25                  30

Tyr Trp Tyr Gln Gln Leu Pro Gly Thr Ala Pro Lys Leu Leu Ile Tyr
        35                  40                  45

Ser Asn Asn Gln Arg Pro Ser Gly Val Pro Asp Arg Phe Ser Gly Ser
    50                  55                  60

Lys Ser Gly Thr Ser Ala Ser Leu Ala Ile Ser Gly Leu Arg Ser Glu
65                  70                  75                  80

Asp Glu Ala Asp Tyr Tyr Cys Gly Ser Trp Asp Ser Ser Leu Ser Ala
                85                  90                  95

Tyr Val Phe Gly Gly Gly Thr Lys Leu Thr Val Leu
            100                 105
```

<210> SEQ ID NO 55
<211> LENGTH: 330
<212> TYPE: DNA
<213> ORGANISM: Artificial Sequence
<220> FEATURE:
<223> OTHER INFORMATION: Nucleotide sequence of light chain variable
      region LC6

<400> SEQUENCE: 55

```
cagtctgtgc tgactcagcc accctcagcg tctgggaccc ccgggcagag ggtcaccatc      60
tcttgtagtg gctcttcatc taatattggc agtaatgctg tcaactggta ccagcagctc     120
ccaggaacgg cccccaaact cctcatctat gctgatagta atcggccaag cggggtccct     180
gaccgattct ctggctccaa gtctggcacc tcagcctccc tggccatcag tgggctccgg     240
tccgaggatg aggctgatta ttactgtggt tcttgggatt atagcctgag tggttatgtc     300
ttcggcggag gcaccaagct gacggtccta                                      330
```

<210> SEQ ID NO 56
<211> LENGTH: 110
<212> TYPE: PRT
<213> ORGANISM: Artificial Sequence
<220> FEATURE:
<223> OTHER INFORMATION: Amino acid sequence of light chain
      variable region LC6

<400> SEQUENCE: 56

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Ala Val Asn Trp Tyr Gln Gln Leu Pro Gly Thr Ala Pro Lys Leu Leu
        35                  40                  45

Ile Tyr Ala Asp Ser Asn Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Ser Trp Asp Tyr Ser Leu
                85                  90                  95

Ser Gly Tyr Val Phe Gly Gly Gly Thr Lys Leu Thr Val Leu
            100                 105                 110

<210> SEQ ID NO 57
<211> LENGTH: 330
<212> TYPE: DNA
<213> ORGANISM: Artificial Sequence
<220> FEATURE:
<223> OTHER INFORMATION: Nucleotide sequence of light chain variable
      region LC7

<400> SEQUENCE: 57
cagtctgtgc tgactcagcc accctcagcg tctgggaccc ccggggcagag ggtcaccatc         60 tcttgtagtg gctcttcatc taatattggc aataattctg tctactggta ccagcagctc        120
ccaggaacgg cccccaaact cctcatctat gctaatagtc atcggccaag cggggtccct        180
gaccgattct ctggctccaa gtctggcacc tcagcctccc tggccatcag tgggctccgg        240
tccgaggatg aggctgatta ttactgtggt acttgggatt atagcctgag tggttatgtc        300
ttaggcggag gcaccaagct gacggtccta                                         330

<210> SEQ ID NO 58
<211> LENGTH: 110
<212> TYPE: PRT
<213> ORGANISM: Artificial Sequence
<220> FEATURE:
<223> OTHER INFORMATION: Amino acid sequence of light chain
      variable region LC7

<400> SEQUENCE: 58

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Asn Asn
            20                  25                  30

Ser Val Tyr Trp Tyr Gln Gln Leu Pro Gly Thr Ala Pro Lys Leu Leu
        35                  40                  45

Ile Tyr Ala Asn Ser His Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Thr Trp Asp Tyr Ser Leu
                85                  90                  95

Ser Gly Tyr Val Leu Gly Gly Gly Thr Lys Leu Thr Val Leu
            100                 105                 110

<210> SEQ ID NO 59
<211> LENGTH: 330
<212> TYPE: DNA
<213> ORGANISM: Artificial Sequence
<220> FEATURE:
<223> OTHER INFORMATION: Nucleotide sequence of light chain variable
      region LC8

<400> SEQUENCE: 59

```
cagtctgtgc tgactcagcc accctcagcg tctgggaccc ccgggcagag ggtcaccatc      60
tcttgtagtg gctcttcatc taatattggc aataatgatg tctcctggta ccagcagctc     120
ccaggaacgg cccccaaact cctcatctat tctgatagtc agcggccaag cggggtcccc     180
gaccgattct ctggctccaa gtctggcacc tcagcctccc tggccatcag tgggctccgg     240
tccgaggatg aggctgatta ttactgtggt tcttgggatg ctagcctgaa tggttatgtc     300
ttcggcggag gcaccaagct gacggtccta                                      330
```

<210> SEQ ID NO 60
<211> LENGTH: 110
<212> TYPE: PRT
<213> ORGANISM: Artificial Sequence
<220> FEATURE:
<223> OTHER INFORMATION: Amino acid sequence of light chain
      variable region LC8

<400> SEQUENCE: 60

```
Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Asn Asn
            20                  25                  30

Asp Val Ser Trp Tyr Gln Gln Leu Pro Gly Thr Ala Pro Lys Leu Leu
        35                  40                  45

Ile Tyr Ser Asp Ser Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Ser Trp Asp Ala Ser Leu
                85                  90                  95

Asn Gly Tyr Val Phe Gly Gly Gly Thr Lys Leu Thr Val Leu
            100                 105                 110
```

<210> SEQ ID NO 61
<211> LENGTH: 330
<212> TYPE: DNA
<213> ORGANISM: Artificial Sequence
<220> FEATURE:
<223> OTHER INFORMATION: Nucleotide sequence of light chain variable
      region LC9

<400> SEQUENCE: 61

```
cagtctgtgc tgactcagcc accctcagcg tctgggaccc ccgggcagag ggtcaccatc      60
tcttgtactg gctcttcatc taatattggc aataatgctg tctcctggta ccagcagctc     120
ccaggaacgg cccccaaact cctcatctat gatgataatc atcggccaag cggggtccct     180
gaccgattct ctggctccaa gtctggcacc tcagcctccc tggccatcag tgggctccgg     240
tccgaggatg aggctgatta ttactgtggt tcttgggatg ctagcctgaa tggttatgtc     300
ttcggcggag gcaccaagct gacggtccta                                      330
```

-continued

<210> SEQ ID NO 62
<211> LENGTH: 110
<212> TYPE: PRT
<213> ORGANISM: Artificial Sequence
<220> FEATURE:
<223> OTHER INFORMATION: Amino acid sequence of light chain
      variable region LC9

<400> SEQUENCE: 62

```
Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Asn Asn
            20                  25                  30

Ala Val Ser Trp Tyr Gln Gln Leu Pro Gly Thr Ala Pro Lys Leu Leu
        35                  40                  45

Ile Tyr Asp Asp Asn His Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Ser Trp Asp Ala Ser Leu
                85                  90                  95

Asn Gly Tyr Val Phe Gly Gly Gly Thr Lys Leu Thr Val Leu
            100                 105                 110
```

<210> SEQ ID NO 63
<211> LENGTH: 330
<212> TYPE: DNA
<213> ORGANISM: Artificial Sequence
<220> FEATURE:
<223> OTHER INFORMATION: Nucleotide sequence of light chain variable
      region LC10

<400> SEQUENCE: 63

```
cagtctgtgc tgactcagcc accctcagcg tctgggaccc ccgggcagag ggtcaccatc    60
tcttgtactg gctcttcatc taatattggc aataatgctg tcacctggta ccagcagctc   120
ccaggaacgg cccccaaact cctcatctat gatgatagtc atcggccaag cggggcccct   180
gaccgattct ctggctccaa gtctggcacc tcagcctccc tggccatcag tgggctccgg   240
tccgaggatg aggctgatta ttactgtggt acttgggatg ctagcctgag tgcttatgtc   300
ttcggcggag gcaccaagct gacggtccta                                    330
```

<210> SEQ ID NO 64
<211> LENGTH: 110
<212> TYPE: PRT
<213> ORGANISM: Artificial Sequence
<220> FEATURE:
<223> OTHER INFORMATION: Amino acid sequence of light chain
      variable region LC10

<400> SEQUENCE: 64

```
Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Asn Asn
            20                  25                  30

Ala Val Thr Trp Tyr Gln Gln Leu Pro Gly Thr Ala Pro Lys Leu Leu
        35                  40                  45

Ile Tyr Asp Asp Ser His Arg Pro Ser Gly Ala Pro Asp Arg Phe Ser
    50                  55                  60

Gly Ser Lys Ser Gly Thr Ser Ala Ser Leu Ala Ile Ser Gly Leu Arg
65                  70                  75                  80
```

```
Ser Glu Asp Glu Ala Asp Tyr Tyr Cys Gly Thr Trp Asp Ala Ser Leu
            85                  90                  95

Ser Ala Tyr Val Phe Gly Gly Gly Thr Lys Leu Thr Val Leu
            100                 105                 110

<210> SEQ ID NO 65
<211> LENGTH: 324
<212> TYPE: DNA
<213> ORGANISM: Artificial Sequence
<220> FEATURE:
<223> OTHER INFORMATION: Nucleotide sequence of light chain variable
      region LC11

<400> SEQUENCE: 65
cagtctgtgc tgactcagcc accctcagcg tctgggaccc ccgggcagag ggtcaccatc    60
tcttgtggcg gcgataacat tccttataaa tatgcggatt ggtaccagca gctcccagga   120
acggccccca aactcctcat ctattctgat aataagcggc caagcggggt ccctgaccga   180
ttctctggct ccaagtctgg cacctcagcc tccctggcca tcagtgggct ccggtccgag   240
gatgaggctg attattactg tgcttcttgg gatgctagcc tgaatggtta tgtcttcggc   300
ggaggcacca agctgacggt ccta                                          324

<210> SEQ ID NO 66
<211> LENGTH: 108
<212> TYPE: PRT
<213> ORGANISM: Artificial Sequence
<220> FEATURE:
<223> OTHER INFORMATION: Amino acid sequence of light chain
      variable region LC11

<400> SEQUENCE: 66

Gln Ser Val Leu Thr Gln Pro Pro Ser Ala Ser Gly Thr Pro Gly Gln
1               5                   10                  15

Arg Val Thr Ile Ser Cys Gly Gly Asp Asn Ile Pro Tyr Lys Tyr Ala
            20                  25                  30

Asp Trp Tyr Gln Gln Leu Pro Gly Thr Ala Pro Lys Leu Leu Ile Tyr
            35                  40                  45

Ser Asp Asn Lys Arg Pro Ser Gly Val Pro Asp Arg Phe Ser Gly Ser
    50                  55                  60

Lys Ser Gly Thr Ser Ala Ser Leu Ala Ile Ser Gly Leu Arg Ser Glu
65                  70                  75                  80

Asp Glu Ala Asp Tyr Tyr Cys Ala Ser Trp Asp Ala Ser Leu Asn Gly
            85                  90                  95

Tyr Val Phe Gly Gly Gly Thr Lys Leu Thr Val Leu
            100                 105

<210> SEQ ID NO 67
<211> LENGTH: 330
<212> TYPE: DNA
<213> ORGANISM: Artificial Sequence
<220> FEATURE:
<223> OTHER INFORMATION: Nucleotide sequence of light chain variable
      region LC12

<400> SEQUENCE: 67
cagtctgtgc tgactcagcc accctcagcg tctgggaccc ccgggcagag ggtcaccatc    60
tcttgtactg gctcttcatc taatattggc aataatgatg tctcctggta ccagcagctc   120
ccaggaacgg cccccaaact cctcatctat gataataatc atcggccaag cggggtccct   180
```

```
gaccgattct ctggctccaa gtctggcacc tcagcctccc tggccatcag tgggctccgg     240
tccgaggatg aggctgatta ttactgtggt acttgggatg ctagcctgaa tggttatgtc     300
ttcggcggag gcaccaagct gacggtccta                                      330
```

<210> SEQ ID NO 68
<211> LENGTH: 110
<212> TYPE: PRT
<213> ORGANISM: Artificial Sequence
<220> FEATURE:
<223> OTHER INFORMATION: Amino acid sequence of light chain
      variable region LC12

<400> SEQUENCE: 68

```
Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Asn Asn
            20                  25                  30

Asp Val Ser Trp Tyr Gln Gln Leu Pro Gly Thr Ala Pro Lys Leu Leu
        35                  40                  45

Ile Tyr Asp Asn Asn His Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Thr Trp Asp Ala Ser Leu
                85                  90                  95

Asn Gly Tyr Val Phe Gly Gly Gly Thr Lys Leu Thr Val Leu
            100                 105                 110
```

<210> SEQ ID NO 69
<211> LENGTH: 330
<212> TYPE: DNA
<213> ORGANISM: Artificial Sequence
<220> FEATURE:
<223> OTHER INFORMATION: Nucleotide sequence of light chain variable
      region LC13

<400> SEQUENCE: 69

```
cagtctgtgc tgactcagcc accctcagcg tctgggaccc ccgggcaggg ggtcaccatc     60
tcttgtactg ctcttcatc taatattggc aataataatg tctactggta ccagcagctc     120
ccaggaacgg ccccaaaact cctcatctat tctgataata tcggccaag cggggtccct     180 gaccgattct ctggctccaa gtctggcacc tcagcctccc tggccatcag tgggctccgg     240
tccgaggatg aggctgatta ttactgtggt gcttgggatg atagcctgag tgcttatgtc     300
ttcggcggag gcaccaagct gacggtccta                                      330
```

<210> SEQ ID NO 70
<211> LENGTH: 110
<212> TYPE: PRT
<213> ORGANISM: Artificial Sequence
<220> FEATURE:
<223> OTHER INFORMATION: Amino acid sequence of light chain
      variable region LC13

<400> SEQUENCE: 70

```
Gln Ser Val Leu Thr Gln Pro Pro Ser Ala Ser Gly Thr Pro Gly Gln
1               5                   10                  15

Gly Val Thr Ile Ser Cys Thr Gly Ser Ser Ser Asn Ile Gly Asn Asn
            20                  25                  30

Asn Val Tyr Trp Tyr Gln Gln Leu Pro Gly Thr Ala Pro Lys Leu Leu
```

```
                35                  40                  45
Ile Tyr Ser Asp Asn Arg Pro Ser Gly Val Pro Asp Arg Phe Ser
            50                  55                  60
Gly Ser Lys Ser Gly Thr Ser Ala Ser Leu Ala Ile Ser Gly Leu Arg
65                  70                  75                  80
Ser Glu Asp Glu Ala Asp Tyr Tyr Cys Gly Ala Trp Asp Ser Leu
                85                  90                  95
Ser Ala Tyr Val Phe Gly Gly Gly Thr Lys Leu Thr Val Leu
                100                 105                 110

<210> SEQ ID NO 71
<211> LENGTH: 330
<212> TYPE: DNA
<213> ORGANISM: Artificial Sequence
<220> FEATURE:
<223> OTHER INFORMATION: Nucleotide sequence of light chain variable
      region LC14

<400> SEQUENCE: 71
cagtctgtgc tgactcagcc accctcagcg tctgggaccc ccgggcagag ggtcaccatc    60
tcttgtagtg gctcttcatc taatattggc agtaatgctg tctactggta ccagcagctc   120
ccaggaacgg cccccaaact cctcatctat gatgatagta agcggccaag cggggtccct   180
gaccgattct ctggctccaa gtctggcacc tcagcctccc tggccatcgg tgggctccgg   240
tccgaggatg aggctgatta ttactgtggt gcttgggatg atagcctgag tgcttatgtc   300
ttcggcggag gcaccaagct gacggtccta                                    330

<210> SEQ ID NO 72
<211> LENGTH: 110
<212> TYPE: PRT
<213> ORGANISM: Artificial Sequence
<220> FEATURE:
<223> OTHER INFORMATION: Amino acid sequence of light chain
      variable region LC14

<400> SEQUENCE: 72

Gln Ser Val Leu Thr Gln Pro Pro Ser Ala Ser Gly Thr Pro Gly Gln
1               5                   10                  15
Arg Val Thr Ile Ser Cys Ser Gly Ser Ser Ser Asn Ile Gly Ser Asn
                20                  25                  30
Ala Val Tyr Trp Tyr Gln Gln Leu Pro Gly Thr Ala Pro Lys Leu Leu
                35                  40                  45
Ile Tyr Asp Asp Ser Lys Arg Pro Ser Gly Val Pro Asp Arg Phe Ser
            50                  55                  60
Gly Ser Lys Ser Gly Thr Ser Ala Ser Leu Ala Ile Gly Gly Leu Arg
65                  70                  75                  80
Ser Glu Asp Glu Ala Asp Tyr Tyr Cys Gly Ala Trp Asp Ser Leu
                85                  90                  95
Ser Ala Tyr Val Phe Gly Gly Gly Thr Lys Leu Thr Val Leu
                100                 105                 110

<210> SEQ ID NO 73
<211> LENGTH: 330
<212> TYPE: DNA
<213> ORGANISM: Artificial Sequence
<220> FEATURE:
<223> OTHER INFORMATION: Nucleotide sequence of light chain variable
      region LC15

<400> SEQUENCE: 73
```

-continued

```
cagtctgtgc tgactcagcc accttcagcg tctgggaccc ccgggcagag ggtcaccatc      60
tcttgtagtg gctcttcatc taatattggc agtaatactg tctactggta ccagcagctc     120
ccaggaacgg cccccaaact cctcatctat gatgataatc atcggccaag cggggtccct     180
gaccgattct ctggctccaa gtctggcacc tcagcctccc tggccatcag tgggctccgg     240
tccgaggatg aggctgatta ttactgtggt gcttgggatg atagcctgag tgcttatgtc     300
ttcggcggag gcaccaagct gacggtccta                                       330
```

<210> SEQ ID NO 74
<211> LENGTH: 110
<212> TYPE: PRT
<213> ORGANISM: Artificial Sequence
<220> FEATURE:
<223> OTHER INFORMATION: Amino acid sequence of light chain
     variable region LC15

<400> SEQUENCE: 74

```
Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Thr Val Tyr Trp Tyr Gln Gln Leu Pro Gly Thr Ala Pro Lys Leu Leu
        35                  40                  45

Ile Tyr Asp Asp Asn His Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Ala Trp Asp Asp Ser Leu
                85                  90                  95

Ser Ala Tyr Val Phe Gly Gly Gly Thr Lys Leu Thr Val Leu
            100                 105                 110
```

<210> SEQ ID NO 75
<211> LENGTH: 330
<212> TYPE: DNA
<213> ORGANISM: Artificial Sequence
<220> FEATURE:
<223> OTHER INFORMATION: Nucleotide sequence of light chain variable
     region LC16

<400> SEQUENCE: 75

```
cagtctgtgc tgactcagcc accctcagcg tctgggaccc ccgggcggag ggtcaccatc      60
tcttgtagtg gctcttcacc taatattggc aataatactg tcaactggta ccagcagctc     120
ccaggaacgg cccccaaact cctcatctat tctgatagtc atcggccaag cggggtccct     180
gaccgattct ctggctccaa gtctggcacc tcagcctccc tggccatcag tgggctccgg     240
tccgaggatg aggctgatta ttactgtggt gcttgggatt atagcctgaa tgcttatgtc     300
ttcggcggag gcaccaagct gacggtccta                                       330
```

<210> SEQ ID NO 76
<211> LENGTH: 110
<212> TYPE: PRT
<213> ORGANISM: Artificial Sequence
<220> FEATURE:
<223> OTHER INFORMATION: Amino acid sequence of light chain
     variable region LC16

<400> SEQUENCE: 76

Gln Ser Val Leu Thr Gln Pro Pro Ser Ala Ser Gly Thr Pro Gly Arg
1               5                   10                  15

Arg Val Thr Ile Ser Cys Ser Gly Ser Ser Pro Asn Ile Gly Asn Asn
            20                  25                  30

Thr Val Asn Trp Tyr Gln Gln Leu Pro Gly Thr Ala Pro Lys Leu Leu
        35                  40                  45

Ile Tyr Ser Asp Ser His Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Ala Trp Asp Tyr Ser Leu
                85                  90                  95

Asn Ala Tyr Val Phe Gly Gly Gly Thr Lys Leu Thr Val Leu
            100                 105                 110

<210> SEQ ID NO 77
<211> LENGTH: 330
<212> TYPE: DNA
<213> ORGANISM: Artificial Sequence
<220> FEATURE:
<223> OTHER INFORMATION: Nucleotide sequence of light chain variable
      region LC17

<400> SEQUENCE: 77
cagtctgtgc tgactcagcc accctcagcg cctgggaccc ccgggcagag ggtcaccatc      60
tcttgtagtg gctcttcatc taatattggc agtaatgctg tcacctggta ccagcagctc     120
ccaggaacgg cccccaaact cctcatctat tatgataata tcggccaag cggggtccct      180 gaccgattct ctggctccaa gtctggcacc tcagcctccc tggccatcag tgggctccgg     240
tccgaggatg aggctgatta ttactgtggt acttgggatt atagcctgag tggttatgtc     300
ttaggcggag gcaccaagct gacggtccta                                      330

<210> SEQ ID NO 78
<211> LENGTH: 110
<212> TYPE: PRT
<213> ORGANISM: Artificial Sequence
<220> FEATURE:
<223> OTHER INFORMATION: Amino acid sequence of light chain
      variable region LC17

<400> SEQUENCE: 78

Gln Ser Val Leu Thr Gln Pro Pro Ser Ala Pro Gly Thr Pro Gly Gln
1               5                   10                  15

Arg Val Thr Ile Ser Cys Ser Gly Ser Ser Ser Asn Ile Gly Ser Asn
            20                  25                  30

Ala Val Thr Trp Tyr Gln Gln Leu Pro Gly Thr Ala Pro Lys Leu Leu
        35                  40                  45

Ile Tyr Tyr Asp Asn Asn Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Thr Trp Asp Tyr Ser Leu
                85                  90                  95

Ser Gly Tyr Val Leu Gly Gly Gly Thr Lys Leu Thr Val Leu
            100                 105                 110

<210> SEQ ID NO 79
<211> LENGTH: 330

<212> TYPE: DNA
<213> ORGANISM: Artificial Sequence
<220> FEATURE:
<223> OTHER INFORMATION: Nucleotide sequence of light chain variable
region LC18

<400> SEQUENCE: 79

```
cagtctgtgc tgactcagcc accctcagcg tctgggaccc ccgggcagag ggtcaccatc      60
tcttgtagtg ctcttcatc taatattggc agtaatgctg tctactggta ccagcagctc     120
ccaggaacgg cccccaaact cctcatctat gatgatagta agcggccaag cggggtccct    180
gaccgattct ctggctccaa gtctggcacc tcagcctccc tggccatcag tgggttccgg    240
tccgaggatg aggctgatta ttactgtggt tcttgggatg ctagcctgaa tgcttatgtc    300
ttcggcggag gcaccaagct gacggtccta                                     330
```

<210> SEQ ID NO 80
<211> LENGTH: 110
<212> TYPE: PRT
<213> ORGANISM: Artificial Sequence
<220> FEATURE:
<223> OTHER INFORMATION: Amino acid sequence of light chain
variable region LC18

<400> SEQUENCE: 80

```
Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Ala Val Tyr Trp Tyr Gln Gln Leu Pro Gly Thr Ala Pro Lys Leu Leu
        35                  40                  45

Ile Tyr Asp Asp Ser Lys Arg Pro Ser Gly Val Pro Asp Arg Phe Ser
    50                  55                  60

Gly Ser Lys Ser Gly Thr Ser Ala Ser Leu Ala Ile Ser Gly Phe Arg
65                  70                  75                  80

Ser Glu Asp Glu Ala Asp Tyr Tyr Cys Gly Ser Trp Asp Ala Ser Leu
                85                  90                  95

Asn Ala Tyr Val Phe Gly Gly Gly Thr Lys Leu Thr Val Leu
            100                 105                 110
```

<210> SEQ ID NO 81
<211> LENGTH: 342
<212> TYPE: DNA
<213> ORGANISM: Artificial Sequence
<220> FEATURE:
<223> OTHER INFORMATION: Nucleotide sequence of light chain variable
region LC19

<400> SEQUENCE: 81

```
gatattgtga tgacccagac tccactctcc ctgcccgtca cccctggaca gccggcctcc      60
atctcctgca ggtctagtca gagcctcttc gatagtgatg atggcaacac ctatttggac    120
tggtacctgc agaagccagg gcagtctcca cagctcctga tctatcgcgt ttcctatcgg    180
gcctctggag tcccagacag gttcagtggc agtgggtcag gcactgattt cacactgaaa    240
atcagcaggg tggaggctgg agattctgga atatattact gcatgcaacg tgtggagttt    300
ccttatactt ttggccaggg gaccaagctg gaaatcaaac gt                       342
```

<210> SEQ ID NO 82
<211> LENGTH: 114
<212> TYPE: PRT

<213> ORGANISM: Artificial Sequence
<220> FEATURE:
<223> OTHER INFORMATION: Amino acid sequence of light chain
      variable region LC19

<400> SEQUENCE: 82

Asp Ile Val Met Thr Gln Thr Pro Leu Ser Leu Pro Val Thr Pro Gly
1               5                   10                  15

Gln Pro Ala Ser Ile Ser Cys Arg Ser Ser Gln Ser Leu Phe Asp Ser
            20                  25                  30

Asp Asp Gly Asn Thr Tyr Leu Asp Trp Tyr Leu Gln Lys Pro Gly Gln
        35                  40                  45

Ser Pro Gln Leu Leu Ile Tyr Ala Leu Ser Tyr Arg Ala Ser Gly Val
    50                  55                  60

Pro Asp Arg Phe Ser Gly Ser Gly Ser Gly Thr Asp Phe Thr Leu Lys
65                  70                  75                  80

Ile Ser Arg Val Glu Ala Gly Asp Ser Gly Ile Tyr Tyr Cys Met Gln
                85                  90                  95

Arg Val Glu Phe Pro Tyr Thr Phe Gly Gln Gly Thr Lys Leu Glu Ile
            100                 105                 110

Lys Arg

<210> SEQ ID NO 83
<211> LENGTH: 324
<212> TYPE: DNA
<213> ORGANISM: Artificial Sequence
<220> FEATURE:
<223> OTHER INFORMATION: Nucleotide sequence of light chain variable
      region LC20

<400> SEQUENCE: 83
tcctatgagc tgactcagcc accctcagtg tcagtggccc caggcaggac ggccacactt     60
acctgtgggg gagataacat tgaacataaa agtgtgcact ggtaccagca gaagccaggc    120
caggccccct tgttgatcat gtattacgat agtgaccggc cctcagggt  cccggagcga    180 ttctctggct ccaactttgg aaacacggcc accctgacca tcgacagggt cgaagccggg    240
gatgaggccg actattattg tcaagtgtgg gataatttta ctgaacatcc ggtgttcggc    300
agagggacca agctgaccgt ccta                                           324

<210> SEQ ID NO 84
<211> LENGTH: 108
<212> TYPE: PRT
<213> ORGANISM: Artificial Sequence
<220> FEATURE:
<223> OTHER INFORMATION: Amino acid sequence of light chain
      variable region LC20

<400> SEQUENCE: 84

Ser Tyr Glu Leu Thr Gln Pro Pro Ser Val Ser Val Ala Pro Gly Arg
1               5                   10                  15

Thr Ala Thr Leu Thr Cys Gly Gly Asp Asn Ile Glu His Lys Ser Val
            20                  25                  30

His Trp Tyr Gln Gln Lys Pro Gly Gln Ala Pro Leu Leu Ile Met Tyr
        35                  40                  45

Tyr Asp Ser Asp Arg Pro Ser Gly Val Pro Glu Arg Phe Ser Gly Ser
    50                  55                  60

Asn Phe Gly Asn Thr Ala Thr Leu Thr Ile Asp Arg Val Glu Ala Gly
65                  70                  75                  80

```
Asp Glu Ala Asp Tyr Tyr Cys Gln Val Trp Asp Asn Phe Thr Glu His
                85                  90                  95

Pro Val Phe Gly Arg Gly Thr Lys Leu Thr Val Leu
            100                 105

<210> SEQ ID NO 85
<211> LENGTH: 324
<212> TYPE: DNA
<213> ORGANISM: Artificial Sequence
<220> FEATURE:
<223> OTHER INFORMATION: Nucleotide sequence of light chain variable
      region LC21

<400> SEQUENCE: 85
tcctatgagc tgacacagcc accctcagtg tcagtggccc caggcaggac ggccacactt      60
acctgtgggg gagataacat tgaacataaa agtgtgcact ggtaccagca gaagccaggc     120
caggccccct tgttggtcat gtattacgat agtgaccggc catcagggat cccggagcga     180
ttctctggct ccaactctgg aaacacagcc actctgacca tcaccagggt cgaagccggg     240
gatgaggccg actattattg tcaagtgtgg gataatttta ctgaacatcc ggtgttcggc     300
ggagggacca agctgaccgt ccta                                            324

<210> SEQ ID NO 86
<211> LENGTH: 108
<212> TYPE: PRT
<213> ORGANISM: Artificial Sequence
<220> FEATURE:
<223> OTHER INFORMATION: Amino acid sequence of light chain
      variable region LC21

<400> SEQUENCE: 86

Ser Tyr Glu Leu Thr Gln Pro Pro Ser Val Ser Val Ala Pro Gly Arg
1               5                   10                  15

Thr Ala Thr Leu Thr Cys Gly Gly Asp Asn Ile Glu His Lys Ser Val
            20                  25                  30

His Trp Tyr Gln Gln Lys Pro Gly Gln Ala Pro Leu Leu Val Met Tyr
        35                  40                  45

Tyr Asp Ser Asp Arg Pro Ser Gly Val Pro Glu Arg Phe Ser Gly Ser
    50                  55                  60

Asn Ser Gly Asn Thr Ala Thr Leu Thr Ile Thr Arg Val Glu Ala Gly
65                  70                  75                  80

Asp Glu Ala Asp Tyr Tyr Cys Gln Val Trp Asp Asn Phe Thr Glu His
                85                  90                  95

Pro Val Phe Gly Gly Gly Thr Lys Leu Thr Val Leu
            100                 105

<210> SEQ ID NO 87
<211> LENGTH: 327
<212> TYPE: DNA
<213> ORGANISM: Artificial Sequence
<220> FEATURE:
<223> OTHER INFORMATION: Nucleotide sequence of light chain variable
      region LC22

<400> SEQUENCE: 87
cagtctgccc tgactcagcc tgcctccgtg tctgggtctc ctggagagtc gatcatcatc      60
tcctgcactg gaaccagcag tgacgttggt gcttataact atgtctcctg gtaccaacag     120
cacctaggca aagcccccaa actcatgatt tatgatgtca gtcagcggcc ctcagggatt     180
tctgatcgct tctctggctc caagtctggc aacacggcct ccctgacaat ctctgggctc     240
```
caggctgagg acgaggccga ttattattgc agctcattca caggtgacag tgttatattc    300
ggcggaggga ccaagctgac cgtccta    327

<210> SEQ ID NO 88
<211> LENGTH: 109
<212> TYPE: PRT
<213> ORGANISM: Artificial Sequence
<220> FEATURE:
<223> OTHER INFORMATION: Amino acid sequence of light chain
      variable region LC22

<400> SEQUENCE: 88

Gln Ser Ala Leu Thr Gln Pro Ala Ser Val Ser Gly Ser Pro Gly Glu
1               5                   10                  15

Ser Ile Ile Ile Ser Cys Thr Gly Thr Ser Ser Asp Val Gly Ala Tyr
            20                  25                  30

Asn Tyr Val Ser Trp Tyr Gln Gln His Leu Gly Lys Ala Pro Lys Leu
        35                  40                  45

Met Ile Tyr Asp Val Ser Gln Arg Pro Ser Gly Val Ser Asp Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Phe Thr Gly Asp
                85                  90                  95

Ser Val Ile Phe Gly Gly Gly Thr Lys Leu Thr Val Leu
            100                 105

<210> SEQ ID NO 89
<211> LENGTH: 330
<212> TYPE: DNA
<213> ORGANISM: Artificial Sequence
<220> FEATURE:
<223> OTHER INFORMATION: Nucleotide sequence of light chain variable
      region LC23

<400> SEQUENCE: 89
cagtctgccc tgactcagcc tcgctcagtg tccgggtctc ctggacagtc agtcaccatt    60
tcttgtactg gatcccgcgg tgacgttgga ggttatgact ttgtctcctg gtaccgtcaa    120
tacccaggcg aggccccca actcattatt tatgatgtca gcggggaggcc atcaggagtc    180 cctgatcgct tctctggctc caagtctggc aacacggcct ccctgaccat ctctgggctc    240
cagcctgaag atgaggctga ttattattgc tcttcatacg ccggcagtga gatttatgtc    300
ttcggaactg ggaccaaggt caccgtccta    330

<210> SEQ ID NO 90
<211> LENGTH: 110
<212> TYPE: PRT
<213> ORGANISM: Artificial Sequence
<220> FEATURE:
<223> OTHER INFORMATION: Amino acid sequence of light chain
      variable region LC23

<400> SEQUENCE: 90

Gln Ser Ala Leu Thr Gln Pro Arg Ser Val Ser Gly Ser Pro Gly Gln
1               5                   10                  15

Ser Val Thr Ile Ser Cys Thr Gly Ser Arg Gly Asp Val Gly Gly Tyr
            20                  25                  30

Asp Phe Val Ser Trp Tyr Arg Gln Tyr Pro Gly Glu Ala Pro Gln Leu
        35                  40                  45

```
Ile Ile Tyr Asp Val Ser Gly Arg Pro Ser Gly Val Pro Asp Arg Phe
        50                  55                  60

Ser Gly Ser Lys Ser Gly Asn Thr Ala Ser Leu Thr Ile Ser Gly Leu
65                  70                  75                  80

Gln Pro Glu Asp Glu Ala Asp Tyr Tyr Cys Ser Ser Tyr Ala Gly Ser
                85                  90                  95

Glu Ile Tyr Val Phe Gly Thr Gly Thr Lys Val Thr Val Leu
            100                 105                 110

<210> SEQ ID NO 91
<211> LENGTH: 339
<212> TYPE: DNA
<213> ORGANISM: Artificial Sequence
<220> FEATURE:
<223> OTHER INFORMATION: Nucleotide sequence of light chain variable
      region LC24

<400> SEQUENCE: 91
gatattgtga tgacccagac tccactctcc tcacatgtca cccttggaca gccggcctcc    60
atatcctgca ggtctagtca gagcctcgta cgcagtgatg caacacgaa cttgagttgg    120 cttcaccaga ggccaggcca gcctccaaga ctcctaattt atacgatttc taaccggttc   180
tctggggtcc cagacagatt cagtggcagt ggggcaggga cagatttcac actgaaaatc   240
agcagggtgg aagctgagga tgtcgggggtt tattactgca tgcaagctac acaatatccg   300
tacacttttg gccaagggac caaggtggag atcaaacgt                           339

<210> SEQ ID NO 92
<211> LENGTH: 113
<212> TYPE: PRT
<213> ORGANISM: Artificial Sequence
<220> FEATURE:
<223> OTHER INFORMATION: Amino acid sequence of light chain
      variable region LC24

<400> SEQUENCE: 92

Asp Ile Val Met Thr Gln Thr Pro Leu Ser Ser His Val Thr Leu Gly
1               5                   10                  15

Gln Pro Ala Ser Ile Ser Cys Arg Ser Ser Gln Ser Leu Val Arg Ser
                20                  25                  30

Asp Gly Asn Thr Asn Leu Ser Trp Leu His Gln Arg Pro Gly Gln Pro
            35                  40                  45

Pro Arg Leu Leu Ile Tyr Thr Ile Ser Asn Arg Phe Ser Gly Val Pro
        50                  55                  60

Asp Arg Phe Ser Gly Ser Gly Ala Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Thr Gln Tyr Pro Tyr Thr Phe Gly Gln Gly Thr Lys Val Glu Ile Lys
            100                 105                 110

Arg

<210> SEQ ID NO 93
<211> LENGTH: 324
<212> TYPE: DNA
<213> ORGANISM: Artificial Sequence
<220> FEATURE:
<223> OTHER INFORMATION: Nucleotide sequence of light chain variable
      region LC25
```

```
<400> SEQUENCE: 93
gacatccaga tgacccagtc tccagccacc ctgtctgtgt ctccagggga aggagccacc        60
ctctcctgca gggccagtca gagtgttacc agcaacttag cctggtacca gcagaaacct       120
ggccaggctc ccaggctcct catctatgat gcatccaaca gggccgctgg catcccagac       180
aggttcagtg gcagtgggtc tgggacagac ttcactctca ccatcagcgg cctagaacct       240
gaagattttg cagtttatta ctgtcagcag cgtgacagct ggcctcaaac ttttggccag       300
gggaccaagc tggagatcaa acgt                                              324

<210> SEQ ID NO 94
<211> LENGTH: 108
<212> TYPE: PRT
<213> ORGANISM: Artificial Sequence
<220> FEATURE:
<223> OTHER INFORMATION: Amino acid sequence of light chain
      variable region LC25

<400> SEQUENCE: 94

Asp Ile Gln Met Thr Gln Ser Pro Ala Thr Leu Ser Val Ser Pro Gly
1               5                   10                  15

Glu Gly Ala Thr Leu Ser Cys Arg Ala Ser Gln Ser Val Thr Ser Asn
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Ala Gly Ile Pro Asp Arg Phe Ser Gly
    50                  55                  60

Ser Gly Ser Gly Thr Asp Phe Thr Leu Thr Ile Ser Gly Leu Glu Pro
65                  70                  75                  80

Glu Asp Phe Ala Val Tyr Tyr Cys Gln Gln Arg Asp Ser Trp Pro Gln
                85                  90                  95

Thr Phe Gly Gln Gly Thr Lys Leu Glu Ile Lys Arg
                100                 105
```

ANTIBODIES AGAINST ANGIOPOIETINS 1 AND 2, AND THEIR USE

CROSS-REFERENCE TO RELATED APPLICATIONS

This application is the U.S. national phase application filed under 35 U.S.C. §371 claiming benefit to International Patent Application No. PCT/KR2011/002338, filed on Apr. 5, 2011, of which application is hereby incorporated herein by reference in its entirety.

TECHNICAL FIELD

The present invention relates to antibodies against angiopoietins 1 and 2, and derivatives of these antibodies. More specifically, the present invention relates therapeutic use of the antibodies and fragments thereof which specifically bind to angiopoietins 1 and 2.

REFERENCE TO SEQUENCE LISTING

The Sequence Listing submitted in the ASCII text file named 204540_0008_00US_602783_ST25.txt is hereby incorporated by reference. The file size is 82 kb and the date of creation is Dec. 3, 2013.

BACKGROUND ART

Angiogenesis is a process of new blood vessels growing from pre-existing vessels. While it is a normal and vital physiological process during growth and development, it is often the transition of tumors from a dormant to a malignant state. In this case, tumor angiogenesis refers to the ability of a tumor to stimulate new blood vessel formation, which is a critical step that enables tumor expansion, local invasion, and dissemination through delivery of oxygen and nutrients, in addition to production of growth factors.

Angiogenesis is a well-controlled process during tumor formation, which is regulated by angiogenic, growth, and survival factors that are secreted by the malignant cells as well as other cells within the tumor microenvironment. Two prominent angiogenic factors include vascular endothelial growth factor (VFGF) family members and angiopoietins.

The angiopoietins are growth factors that modulate the processes of physiological angiogenesis and pathological neovascularization. They signal through Tie-2, a tyrosine receptor kinase present in endothelial cells. Angiopoietin family proteins in human so far include angiopoetin 1, angiopoietin 2, angiopoietin 4, angiopoietin like protein 1 (angiopoitein 3), angiopoietin like protein 2, angiopoietin like protein 3 (angiopoietin 5), angiopoietin like protein 4, angiopoietin like protein 5, angiopoietin like protein 6 and angiopoietin like protein 7.

The role of angiopoietins 1 (Ang1) and 2 (Ang2) in angiogenesis has been implicated by multiple reports. Both angiopoietins 1 and 2 are expressed at tumor vasculature (Stratmann et al., 1998). Coexpression of Ang1 and VEGF-A had an additive effect on angiogenesis and resulted in leakage resistant vessels (Thurston et al., 1999). Mice deficient of Ang1 had impaired vascular function, leading to embryonic death of the mice (Suri et al., 1996) while transgenic overexpression or gene transfer of angiopoietin 1 enhances vessel formation (Suri et al., 1998). Tie-2 knock-out mice showed similar phenotypes of the knock-out mice of angiopoietin 1, which suggests that Tie-2 activation by angiopoietin 1 mediates remodeling and stabilization of developing vessels (Suri et al., 1996).

Angiopoietin 2 is expressed only at sites of vascular remodeling in humans, such as placenta, ovary and uterus. It is mainly secreted by endothelial cells at the sites of vascular remodeling and acts in an autocrine manner. In the presence of VEGF-A, Angiopoietin 2 promotes vascular sprouting and destabilizes blood vessels by disrupting interactions between endothelial cells and matrix, thus enhancing VEGF stimulation (Holash et al., 1999). Angiopoietin 2 also can act as an apoptosis survival factor for endothelialcells during serum deprivation (Kim et al., 2000). Furthermore, upregulation of Angiopoietin 2 correlates with the metastasis and malignancy of various types of human cancers such as breast cancer, metastatic melanoma and lung cancer (Schliemann et al., 2007; Scholz et al., 2007; Park et al., 2007). Local production of Angiopoietin-2 has been identified as an early marker of glioma- and glioblastoma-induced neovascularization (Zagzag et al., 1999; Stratmann et al., 1998). More interestingly, upregulation of angiopoietins 1 and 2 has been shown to be a part of "angiogenic rescue" when VEGF mediated angiogenesis is blocked during tumor progression, resulting in acceleration of metastasis (Casanovas et al., 2005; Ebos et al., 2009; Huang et al., 2009; Paez-Ribes et al., 2009).

Given the role of angiopoietins 1 and 2 in angiogenesis, therapeutics against angiopoietins 1 and 2 might provide a benefit to patients with cancer such as, but not limited to, leukemia, lymphoma, and solid cancers, as well as to other non-neoplastic angiogenesis diseases such as, but not limited to, retinopathies, arthritis, atherosclerosis, respiratory disease, obesity, diabetes, asthma, liver regeneration, pulmonary hypertension, and psoriasis.

DISCLOSURE OF INVENTION

Technical Problem

The object of present invention is to provide antibodies against angiopoietins 1 and 2.

Another object of the present invention is to provide isolated nucleic acids molecules encoding the antibody against angiopoietin 1 and 2.

It is still another object of the present invention to provide recombinant vectors, host cells, isolated cell lines, and hybridomas for the production of such antibodies.

It is still another object of the present invention to provide pharmaceutical compositions containing the antibodies.

It is still another object of the present invention to provide methods for treating cancer, angiogenesis related diseases such as retinopathies, arthritis, psoriasis and related disease using these antibodies.

Solution to Problem

One aspect of the present invention relates to isolated antibodies, antigen-binding portions or derivatives thereof, that specifically bind to angiopoietins 1 and 2.

In one embodiment, the present invention provides an isolated antibody, an antigen-binding portion or a derivative thereof, comprising:

(a) a first CDR set, CDR1, CDR2 and CDR3, that comprise the amino acid sequences of heavy chain CDRs, CDR1, CDR2 and CDR3, that are included in the amino acid sequence as set forth in any one of SEQ ID Nos. 2, 4, 6, 8, 10, 12, 14, 16, 18, 20, 22, 24, 26, 28, 30, 32, 34, 36, 38, 40, 42, and 44;

(b) a second CDR set, CDR1, CDR2 and CDR3, that comprises the amino acid sequences of light chain CDRs, CDR1, CDR2 and CDR3, that are included in the amino acid sequence set forth in any one of SEQ ID Nos. 46, 48, 50, 52, 54, 56, 58, 60, 62, 64, 66, 68, 70, 72, 74, 76, 78, 80, 82, 84, 86, 88, 90, 92 and 94; or, (c) a combination of the first CDR set of (a) and the second CDR set of (b).

In another embodiment, the antibody of the present invention is comprising a heavy chain, a light chain or both of them, wherein said heavy chain comprises a heavy chain variable region having the amino acid sequence as set forth in any one of SEQ ID Nos. 2, 4, 6, 8, 10, 12, 14, 16, 18, 20, 22, 24, 26, 28, 30, 32, 34, 36, 38, 40, 42, and 44, or antigen-binding fragments thereof; and said light chain comprises a light chain variable region having the amino acid sequence as set forth in any one of SEQ ID Nos. 46, 48, 50, 52, 54, 56, 58, 60, 62, 64, 66, 68, 70, 72, 74, 76, 78, 80, 82, 84, 86, 88, 90, 92 and 94, or antigen-binding fragments thereof.

In another embodiment, the antibody of the present invention is selected from the group consisting of:

(i) an antibody comprising the amino acid sequences as set forth in SEQ ID NO:2 and SEQ ID NO:46;

(ii) an antibody comprising the amino acid sequences as set forth in SEQ ID NO:8 and SEQ ID NO:52;

(iii) an antibody comprising the amino acid sequences as set forth in SEQ ID NO:22 and SEQ ID NO:64;

(iv) an antibody comprising the amino acid sequences as set forth in SEQ ID NO:20 and SEQ ID NO:88; and, (v) an antibody comprising the amino acid sequences as set forth in SEQ ID NO:20 and SEQ ID NO:90;

In another aspect, the present invention relates to an isolated antibody, an antigen-binding portion or a derivative thereof, which competes for binding to angiopoietins 1 and 2 with an antibody comprising the amino acid sequence as set forth in any one of SEQ ID NOs: 2, 4, 6, 8, 10, 12, 14, 16, 18, 20, 22, 24, 26, 28, 30, 32, 34, 36, 38, 40, 42, and 44 in combination with the amino acid sequence as set forth in any one of SEQ ID NOs: 46, 48, 50, 52, 54, 56, 58, 60, 62, 64, 66, 68, 70, 72, 74, 76, 78, 80, 82, 84, 86, 88, 90, 92, and 94.

In one embodiment, the isolated antigen binding agent binds to the human angiopoietins 1 and 2 with substantially high affinity such as $K_d$ of less than 10 nM, or competes for binding of angiopoietins 1 and 2 to the receptor with $IC_{50}$ values less than 10 nM.

In another aspect, the present invention relates to an isolated antibody, an antigen-binding portion or a derivative thereof, comprising:

(a) a first CDR set, CDR1, CDR2 and CDR3, that sequentially together are at least 95% identical in amino acid sequence to heavy chain CDRs, CDR1, CDR2 and CDR3, sequentially together, that are included in the amino acid sequence as set forth in any one of SEQ ID Nos. 2, 4, 6, 8, 10, 12, 14, 16, 18, 20, 22, 24, 26, 28, 30, 32, 34, 36, 38, 40, 42, and 44;

(b) a second CDR set, CDR1, CDR2 and CDR3, that sequentially together are at least 95% identical in amino acid sequence to light chain CDRs, CDR1, CDR2 and CDR3, sequentially together, that are included in the amino acid sequence set forth in any one of SEQ ID Nos. 46, 48, 50, 52, 54, 56, 58, 60, 62, 64, 66, 68, 70, 72, 74, 76, 78, 80, 82, 84, 86, 88, 90, 92 and 94; or, (c) a combination of the first CDR set of (a) and the second CDR set of (b),wherein said antibody, antigen-binding portion or derivative competes for angiopoietin binding to angiopoietins 1 and 2.

The antibody may comprise a heavy chain comprising a variable region comprising an amino acid sequence at least 85%, preferably 90%, more preferably 95%, and most preferably 99% identical to the amino acid sequence selected from SEQ ID No. 2, 4, 6, 8, 10, 12, 14, 16, 18, 20, 22, 24, 26, 28, 30, 32, 34, 36, 38, 40, 42 or 44. Further, the antibody may comprise a light chain comprising a variable region comprising an amino acid sequence at least 85%, preferably 90%, more preferably 95%, and most preferably 99% identical to the amino acid sequence selected from SEQ ID No. 46, 48, 50, 52, 54, 56, 58, 60, 62, 64, 66, 68, 70, 72, 74, 76, 78, 80, 82, 84, 86, 88, 90, 92 and 94.

In another aspect, the present invention provides an isolated antibody, an antigen binding portion or a derivative thereof, comprising an amino acid sequence selected from the group consisting of:

(a) a heavy chain CDR3 sequence that differs by no more than a total of three amino acid additions, deletions, and/or non-conservative substitutions from a CDR3 sequence selected from SEQ ID Nos. 2, 4, 6, 8, 10, 12, 14, 16, 18, 20, 22, 24, 26, 28, 30, 32, 34, 36, 38, 40, 42 and 44;

(b) a light chain CDR3 sequence that differs by no more than a total of three amino acid additions, deletions, and/or non-conservative substitutions from a CDR3 sequence selected from SEQ ID Nos. 46, 48, 50, 52, 54, 56, 58, 60, 62, 64, 66, 68, 70, 72, 74, 76, 78, 80, 82, 84, 86, 88, 90, 92 and 94; and, (c) a combination of a heavy chain CDR3 sequence of (a) and the light chain CDR3 sequence of (b), wherein said antibody or antigen binding portion binds to angiopoietins 1 and 2. In one embodiment, the isolated antibody, antigen-binding portion or derivative is a monoclonal antibody.

In another embodiment, the isolated antibody, antigen-binding portion or derivative is selected from the group consisting of a human antibody, a humanized antibody, an antigen-binding antibody fragment, a single chain antibody, a diabody, a triabody, a tetrabody, a $F_{ab}$ fragment, a $F_{(ab')2}$ fragment, $F_d$, $scF_v$, a domain antibody, bispecific antibodies, a minibody, a scab, an IgD antibody, an IgE antibody, an IgM antibody, an IgG1 antibody, an IgG2 antibody, an Ig3 antibody, an IgG4 antibody, any derivatives of antibody constant domain, and artificial antibodies based upon protein scaffolds.

In another embodiment, the isolated antibody, antigen-binding portion or derivative is fused to other polypeptides or linked to other chemicals.

Another aspect of the present invention relates to a pharmaceutical composition including an antibody or functional fragment thereof, and a pharmaceutically acceptable carrier. Compositions of the invention comprise the heavy and/or light chain, the variable domains thereof, or antigen-binding portions thereof, or nucleic acid molecules encoding the antibody, antibody chain, or variable domain thereof, and a mixture with one or more pharmaceutically acceptable carrier or fusion partner. Compositions of the invention may further comprise another component, such as a therapeutic agent or a diagnostic agent.

Another aspect of the present invention relates to an isolated nucleic acid comprising a polynucleotide sequence encoding the light chain variable domain, the heavy chain variable domain, or both, of the antibody. The nucleic acid may comprise the nucleotide sequence as set forth in one or more of SEQ ID Nos. 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, and 93.

A further aspect of the present invention relates to a recombinant expression vector, comprising the nucleic acid of reference sequences.

Still a further aspect of the present invention relates to a host cell transformed with the vector.

Still a further aspect of the present invention relates to an isolated cell line, which produces the antibody, or the heavy chain or light chain or an antigen-binding portion thereof.

Still a further aspect of the present invention relates to a hybridoma producing the antibody, or the heavy chain or light chain or an antigen-binding portion thereof.

Still a further aspect of the present invention relates to a method for treating, preventing or inhibiting type II cancer, dyslipodemia, or a related disease in a subject in need thereof, comprising the step of administering to the subject the antibody, the antigen-binding portion or the derivative thereof, or the pharmaceutical composition. The angiopoietins 1 and 2 antibodies can be administered alone, or in combination with additional antibodies or other medicines.

ADVANTAGEOUS EFFECTS OF INVENTION

This invention provides compositions and methods based on interfering with the action of angiopoetins in inducing angiogenesis. Antagonists of the invention, as described herein, provide important therapeutic and diagnostic agents for use in targeting pathological conditions associated with angiogenesis induced by angiopoietins. Accordingly, the invention provides methods, compositions, kits, and articles of manufacture related to modulating angiopoietins 1 and 2 pathway.

BEST MODE FOR CARRYING OUT THE INVENTION

Figure 1A:
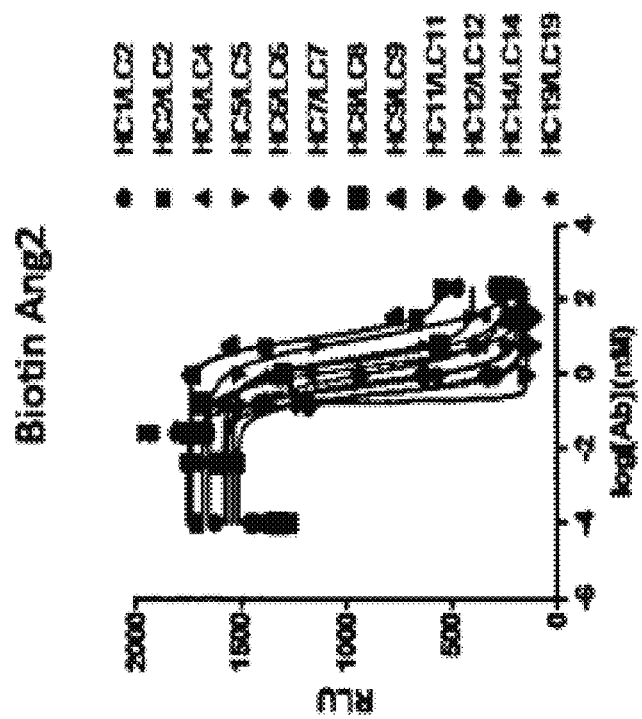
FIG. 1 shows the result of competition EILSA of IgG clones converted from scFv phages, wherein many antibodies blocked the binding of angiopoietins 1 (A) and 2 (B) to Tie-2.

The present invention provides isolated recombinant and/or synthetic antibodies against angiopoietins 1 and 2, as well as compositions and nucleic acid molecules comprising at least one polynucleotide encoding at least one anti-angiopoietins 1 and 2 antibody. This invention provides compositions and methods based on, but not limited to, interfering with angiopoietins 1 and 2 signaling by binding to the binding domain of Tie-2. Antagonists of the invention, as described herein, provide important therapeutic and diagnostic agents for use in targeting pathological conditions associated with cancer mellitus and related disease. Accordingly, the invention provides methods, compositions, kits, and articles of manufacture related to modulating angiopoietins 1 and 2 pathway.

The term, 'an antibody,' as used herein, means a protein consisting of one or more polypeptides substantially encoded by all or part of the recognized immunoglobulin genes. The recognized immunoglobulin genes, for example in humans, include the kappa, lambda, and heavy chain genetic loci, which together comprise the myriad variable region genes, and the constant region genes. Herein, 'antibody' may mean 'a specific antigen binding agent.' A skilled person in the art would readily appreciate that the antibody can be used as a therapeutic or diagnostic agent, and thus, 'antibody' may also be referred to as 'a therapeutic agent' or 'a diagnostic agent.'

An 'isolated antibody,' as used herein, is intended to refer to an antibody that is substantially free of other antibodies having different antigenic specificities (e.g., an isolated antibody that specifically binds angiopoietins 1 and 2 is substantially free of antibodies that specifically bind antigens other than angiopoietins 1 and 2). An isolated antibody that specifically binds angiopoietins 1 and 2 may, however, have cross-reactivity to other antigens, such as angiopoietins 1 and 2 from other species. Moreover, an isolated antibody may be substantially free of other cellular material and/or chemicals. Further, an isolated antibody, e.g., an isolated human antibody, can be a chimeric antibody wherein, e.g., variable regions, CDR domains, or isotypes derived from a different human source are grafted to the parent human antibody. An isolated antibody can also be a humanized antibody, which can be generated, for example, by inserting CDRs of non-human antibodies in the framework sequences of human antibodies.

The term, 'conservative amino acid substitutions,' as used herein, are substitutions that replace an amino acid residue with one imparting similar or better (for the intended purpose) functional and/or chemical characteristics, as one of ordinary skill in the art will appreciate. Conservative amino acid substitutions are often ones in which the amino acid residue is replaced with an amino acid residue with a similar side chain. Families of amino acid residues having similar side chains have been defined in the art. For examples, lysine, arginine, histidine for basic side chains, aspartic acid and glutamic acid for acidic side chains, glycine, asparagines, glutamine, serine, threonine, tyrosine, cysteine, tryptophan for uncharged polar side chains, alanine, valine, leucine, threonine, isoleucine, proline, phenylalanine, methionine for non-polar side chains, and tyrosine, phenylalanine, tryptophan, histidine for aromatic side chains. The substitution is of amino acids with generally similar physiochemical properties such that the substitutions do not substantially alter peptide, polypeptide or protein characteristics, or activity.

Percent identity between two amino acid sequences is a function of the number of amino acid positions shared by the sequences (i.e. a number of the positions with the same amino acid divided by total number of positions multiplied by 100), taking into account the number of gaps, and length of each gap, which need to be introduced for optimal alignment of the two sequences. Antibodies of the present invention also include those in which modification have been made to the framework residues within $V_H$ and/or $V_L$ to improve one of more properties of the antibody. Typically, such framework modifications are made to decrease the immunogenecity or improve the stability of the antibody.

In addition to modifications made within the framework or CDR regions, antibodies of the invention may be engineered to include modifications within the $F_c$ region, typically to alter one or more functional properties of the antibody, such as serum half life, complement fixation, Fc receptor binding, and/or antigen dependent cellular cytotoxicity. Antibody fragments or derived agents are a part of antibodies or antibodies in a different format comprising a portion that binds to an antigen, and optionally, a scaffold or framework portion that allows the antigen-binding portion of the antigen-binding protein to the antigen. For example, changes in framework or CDR, such as amino acid substitutions, deletions, or additions, can be made yet to maintain its antigen-binding ability. Alternatively, antigen-binding portion of the invention can be derivatized, linked or recombinantly fused to another molecule (e.g., another peptide, protein, polymers, or chemicals).

Antigen-binding portion of antibodies can be modified to a single chain antibody, a diabody, a triabody, a tetrabody, an isolated $V_L$ or $V_H$ fragment, a $V_{hh}$ fragment, a $F_{ab}$ fragment (monovalent fragment with $V_L$, $C_L$, $V_H$, and $C_{H1}$), a $F_{(ab')2}$ fragment (two $F_{ab}$ fragments linked by a disulfide bridge), $F_d$ ($V_H$ and $C_{H1}$ domains), scF$_v$ ($V_L$ and $V_H$ is joined by a linker), a domain antibody, bispecific antibodies, a minibody, a scab (an antibody fragment containing $V_H$ and $V_L$ as well as either $C_L$ or $C_{H1}$), an IgD antibody, an IgE antibody, an IgM antibody, an IgG1 antibody, an IgG2 antibody, an Ig3 antibody, an IgG4 antibody, or any derivatives of antibody constant domain, and artificial antibodies based upon protein scaffolds, including, but not limited to, fibronectin type, avimers, or cytochrome B.

In one aspect, the present invention provides anti-angiopoietins 1 and 2 therapeutic agents suitable for therapeutic use and capable of effecting varying degrees of disruption of the angiopoietins 1 and 2 signaling pathway.

The present invention provides human antibodies against angiopoietins 1 and 2, and derivatives and fragments thereof, comprising a sequence of polynucleotides that encode all or a portion of a polypeptide that binds to the angiopoietins 1 and 2, such as nucleic acid encoding all or part of an anti-angiopoietins 1 and 2 antibody, antibody fragment, or antibody derivative.

In one embodiment, an antibody of the invention is a human antibody that inhibits binding of human angiopoietins 1 and 2 to receptor Tie-2. For example, an antibody of the invention inhibits angiopoietin1 and/or 2 binding with Tie-2 with an IC$_{50}$ value of-less than 1 uM, preferably less than 100 nM, more preferably less than 10 nM, and most preferably less than 1 nM.

In another embodiment, the present invention provides isolated angiopoietins 1 and 2 specific antibody molecules which comprise heavy and/or light chain variable regions comprising amino acid sequences that are homologous to the corresponding amino acid sequences of the disclosed antibodies, wherein the antibody molecules inhibit angiopoietins 1 and 2 mediated signaling through Tie-2.

For example, the heavy chain variable domain may comprise a sequence of amino acids that is at least 95, 97 or 99% identical to the sequence of a heavy chain variable domain selected from the group consisting of SEQ ID Nos. 2, 4, 6, 8, 10, 12, 14, 16, 18, 20, 22, 24, 26, 28, 30, 32, 34, 36, 38, 40, 42 and 44. Further, the light chain variable domain may comprise a sequence of amino acids that is at least 95, 97 or 99% identical to the sequence of a light chain variable domain selected from the group consisting of SEQ ID Nos. 46, 48, 50, 52, 54, 56, 58, 60, 62, 64, 66, 68, 70, 72, 74, 76, 78, 80, 82, 84, 86, 88, 90, 92 and 94. Specific embodiments are antagonists which comprise heavy and/or light chain variable regions which are at least 95%, more preferably 97%, and most preferably 99% homologous to disclosed heavy and/or light chain variable regions, respectively.

In another embodiment, the isolated antigen-binding protein comprises a combination of a light chain variable domain and a heavy chain variable domain selected from the group of combinations consisting of a heavy and light chain in SEQ ID Nos.

In a specific embodiment, the present invention provides isolated antibody molecules comprising of the heavy and/or light chain variable domain sequences depicted in SEQ ID Nos. 2, 4, 6, 8, 10, 12, 14, 16, 46, 48, 50, 52, 54, 56, 58, 60, 62, 64, 66, 68, 70, 72, 74, 76, 78, 80, 82, 84, 86, 88, 90, 92 and 94, and conservative modifications thereof.

In another embodiment, this invention includes antibodies that can be formed by any combination of the variable domains from each light chain and heavy chain sequence as shown in SEQ ID Nos. 2, 4, 6, 8, 10, 12, 14, 16, 46, 48, 50, 52, 54, 56, 58, 60, 62, 64, 66, 68, 70, 72, 74, 76, 78, 80, 82, 84, 86, 88, 90, 92 and 94, and equivalents thereof characterized by having one or more conservative amino acid substitutions in any one or more of the CDR sequences, specific embodiments of which inhibit angiopoietins 1 and 2 dependent activation of Tie-2 signaling.

The invention also provides chimeric molecules comprising angiopoietins 1 and 2 antagonist linked or fused to another, heterologous polypeptide or polymer. For instance, techniques are known for deriving an antibody of a different subclass or isotype from an antibody of interest, i.e., subclass switching. These include a humanized antibody, chimeric antibody, a monoclonal antibody, a polyclonal antibody, a recombinant antibody, an antigen-binding antibody fragment such as $F_{(ab')2}$, $F_{ab}$, $F_v$, $F_{ab'}$, $F_c$, and $F_d$ fragments, and can be incorporated into single domain antibodies, such as single chain antibodies, maxibodies, minibodies, intrabodies, diabodies, triabodies, tetrabodioes, v-NAR and bis-scF$_v$ (Hollinger and Hudson, P. J., 2005).

In additional embodiments, antibodies, fragments, and derivatives of the invention can be fused to other polypeptides or chemicals. The fusion partner can be a peptide, a protein, or a derivative of an antibody that has specific binding activity to other proteins to create bispecific or multispecific molecules or to improve the physiochemical properties of the molecules.

In addition, antibodies can be modified to be glycosylated, pegylated, crosslinked, or conjugated to other proteins or chemicals. Amino acids of antibodies can be substituted by non-natural amino acids.

Angiopoietins 1 and 2 antibodies may carry or be conjugated or recombinantly fused to a toxin, radioactive isotope, radionuclide, a liposome, a targeting moiety, a biosensor, a cationic tail, or an enzyme. Such antagonist compositions form an additional aspect of the present invention.

It may be advantageous to have angiopoietins 1 and 2 antagonist antibody that does not interfere with binding of the receptor. Accordingly, in one embodiment, the invention provides an antibody that does not bind Tie-2 binding site on angiopoietins 1 and 2. In another embodiment, an antibody of the invention does not substantially inhibit angiopoietins 1 and 2 binding to Tie-2. In another embodiment, an antibody of the invention does not substantially compete with Tie-2 for binding to angiopoietins 1 and 2.

In another aspect, the present invention provides use of angiopoietins 1 and 2 antagonist antibody of the invention in the preparation of a medicament for the therapeutic and/or prophylactic treatment of angiogenesis related diseases, such as cancer.

In another aspect, the present invention provides use of an expression vector of the invention in the preparation of a medicament for the therapeutic and/or prophylactic treatment of angiogenesis related diseases, such as cancer.

In a further aspect, the present invention provides use of a host cell of the invention in the preparation of a medicament for the therapeutic and/or prophylactic treatment of angiogenesis related diseases, such as cancer.

In still a further aspect, the present invention provides use of an article of manufacture of the invention in the preparation of a medicament for the therapeutic and/or prophylactic treatment of angiogenesis related diseases such as cancer.

The present invention also provides pharmaceutical compositions comprising an antibody, or antigen-binding portion thereof, of the invention and a pharmaceutically acceptable carrier. In one embodiment, the pharmaceutical composition further comprises at least one additional therapeutic agent for treating a disorder in which angiopoietins 1 and 2 overexpression and/or activation is detrimental. The antibodies and antigen-binding portions of the invention can be incorporated into pharmaceutical compositions suitable for administration to a subject. Typically, the pharmaceutical composition comprises an antibody or antigen-binding portion of the invention and a pharmaceutically acceptable carrier.

As used herein, "pharmaceutically acceptable carrier" includes any and all solvents, dispersion media, coatings, antibacterial and antifungal agents, isotonic and absorption delaying agents, and the like that are physiologically compatible. Examples of pharmaceutically acceptable carriers include one or more of water, saline, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition. Pharmaceutically acceptable carriers may further comprise minor amounts of auxiliary substances such as wetting or emulsifying agents, for example, Tweens and other detergents, or preservatives or buffers, which enhance the shelf life or effectiveness of the antibody or antigen-binding portion.

The compositions of this invention may be in a variety of forms. These include, for example, liquid, semi-solid and solid dosage forms, such as liquid solutions (e.g., injectable and infusible solutions), dispersions or suspensions, tablets, pills, powders, liposomes and suppositories. The preferred form depends on the intended mode of administration and therapeutic application. Typical preferred compositions are in the form of injectable or infusible solutions, such as compositions similar to those used for passive immunization of humans with other antibodies.

The antibodies and antigen-binding portions of the present invention can be administered by a variety of methods known in the art, although for many therapeutic applications, the preferred route/mode of administration is subcutaneous injection, intravenous injection or infusion. As will be appreciated by the skilled artisan, the route and/or mode of administration will vary depending upon the desired results.

Supplementary active compounds can also be incorporated into the compositions. In certain embodiments, an antibody or antigen-binding portion of the invention is co-formulated with and/or co-administered with one or more additional therapeutic agents that are useful for treating disorders in which angiopoietins 1 and 2 activation is detrimental. For example, an anti-angiopoietins 1 and 2 antibody or antigen-binding portion of the invention may be co-formulated and/or co-administered with one or more additional antibodies that bind other targets. Furthermore, one or more antibodies of the invention may be used in combination with two or more of therapeutic agents. Such combination therapies may advantageously utilize lower dosages of the administered therapeutic agents, thus avoiding possible toxicities or complications associated with the various monotherapies.

The pharmaceutical compositions of the invention may include a "therapeutically effective amount" or a "prophylactically effective amount" of an antibody or antigen-binding portion of the invention. A "therapeutically effective amount" refers to an amount effective, at dosages and for periods of time necessary, to achieve the desired therapeutic result. A therapeutically effective amount of the antibody or antigen-binding portion may vary according to factors such as the disease state, age, sex, and weight of the individual, and the ability of the antibody or antigen-binding portion to elicit a desired response in the individual. A therapeutically effective amount is also one in which any toxic or detrimental effects of the antibody or antigen-binding portion are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

An exemplary, non-limiting range for a therapeutically or prophylactically effective amount of an antibody or antigen-binding portion of the invention is 0.01-100 mg/kg, more preferably 0.1-30 mg/kg. It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

Practical and presently preferred embodiments of the present invention are illustrative as shown in the following Examples. However, it will be appreciated that those skilled in the art, on consideration of this disclosure, may make modifications and improvements within the spirit and scope of the present invention.

EXAMPLE 1

Screening of Antibodies that Bind to Angiopoietins 1 and 2

Two different phage display libraries were used in the screening. One is generated synthetically in VH3-23 (DP47) and human lambda framework Vλ1g (DPL3) with diverse CDR sequences (Yang et al, 2009) in scFv format. The other library is naive scFv which was generated from human cDNA. For biopanning, biotinylated angiopoietin 1 (R&D Systems) was coated onto Nunc-Immuno™ Maxisorp™ tubes at 10 ug/ml concentration that were preincubated with streptavidin (Pierce) in PBS overnight. After blocking and negative selection, phage libraries displaying scFv of human antibodies were added to the tubes. Followed by 10 washes in PBS containing 0.01% Tween-20, bound phages were eluted with 0.1 M triethylamine. Phage ELISA was performed to select phages that bind both angiopoietins 1 and 2. The phages were then tested for ability to inhibit the interaction of biotinylated angiopoietins 1 and 2 to Tie-2.

Many phages showed strong binding to both angiopoietins 1 and 2.

EXAMPLE 2

Test of Antibodies for their Ability to Block the Interaction Between Angiopoietins 1 and 2 and Tie-2

Selected phage clones that bind to angiopoietins 1 and 2 were sequenced and unique clones were converted into human IgG1 to produce fully human antibodies by transient expression. Conditioned media was harvested and antibodies were purified using protein A agarose beads (Pierce). Various amounts of antibodies were then prepared for competition ELISA to test the ability of antibodies to block binding of biotinylated angiopoietins 1 and 2 to Tie-2.

Figure 1B:
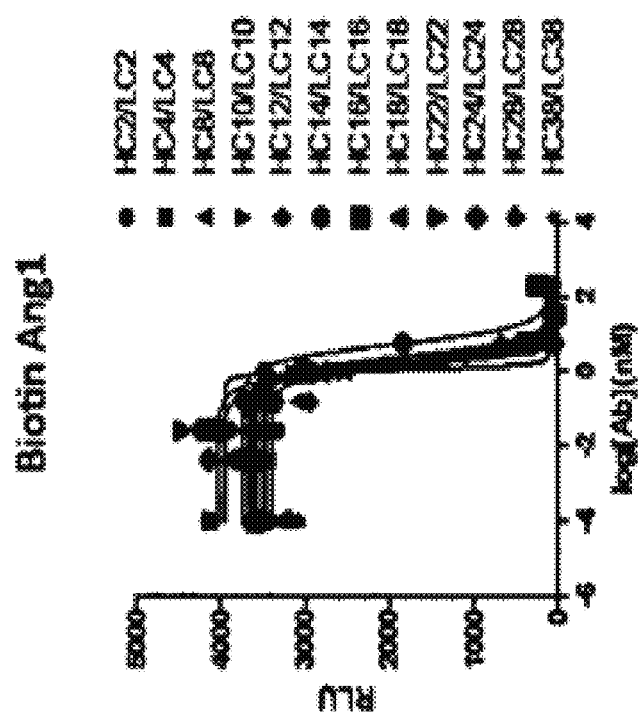

Briefly, various concentrations of antibodies were incubated with biotinylated angiopoietin 1 or 2 and added to the plates coated with Tie2-Fc (R&D Systems). Biotinylated angiopoietin 1 or 2 that was bound to Tie-2 was detected by streptavidin-HRP (Pierce). Many of the antibodies effectively blocked the binding of angiopoietins 1 (FIG. 1A) and 2 to (FIG. 1B) Tie 2.

$IC_{50}$ values were calculated using Graphpad Prism software (Table 1). Many antibodies inhibited the binding of angiopoietins 1 and 2 to Tie-2 at concentrations of $IC_{50}$ value below 1 nM.

TABLE 1

$IC_{50}$ values of antibodies against angiopoietins 1 and 2

| Antibody | $IC_{50}$ against Ang 1 (nM) | $IC_{50}$ against Ang 2 (nM) |
|---|---|---|
| HC2/LC2 | 0.23 | 0.06 |
| HC4/LC4 | 0.26 | 1.353 |
| HC8/LC8 | 0.21 | 0.20 |
| HC10/LC10 | 0.19 | 1.22 |
| HC12/LC12 | 0.38 | 0.04 |
| HC14/LC14 | 0.74 | 0.08 |
| HC16/LC16 | 0.26 | 0.32 |
| HC18/LC18 | 0.24 | 2.85 |
| HC22/LC22 | 0.24 | 0.03 |

EXAMPLE 3

In Vivo Efficacy Test of Antibodies in Xenograft Model

Figure 2A:
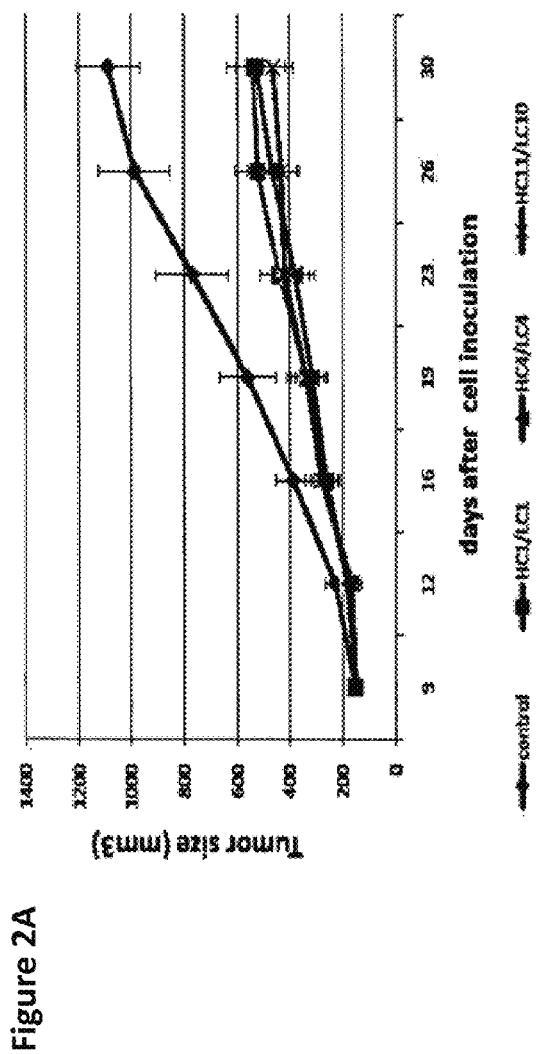
FIG. 2 shows tumor volume (A) and weight (B) from Colo205 xenograft study with the selected antibodies.
Figure 2B:
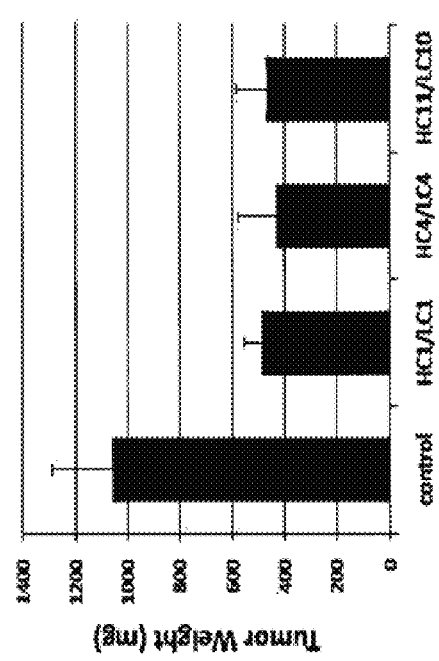

For xenograft model, $5 \times 10^6$ Colo205 cells were injected subcutaneously into 6 ~7 week-old BALB/c nude female mice. When the tumor reached a size of 150-250 mm$^3$, the monoclonal antibodies were injected at a concentration of 10 mg/kg twice a week for three weeks intraperitoneally. Tumor size and body weight was measured twice a week. Serial tumor volumes were calculated by the formula $V(mm^3)=A \times B^2$, with A as the largest dimension and B as the perpendicular diameter. The results were reported as mean ±standard error means. At the end of the experiment, tumor xenografts were recovered from mice, and the weight was measured. Subsequently the tumors were fixed in 4% formaldehyde, and embedded in paraffin. Of the antibodies tested in this example (HC1/LC1, HC4/LC4, HC11/LC10), all three inhibited tumor growth in vivo (FIG. 2).

INDUSTRIAL APPLICABILITY

The present invention relates to pharmaceutical compositions comprising an antibody or antigen-binding portion against angiopoietin 1 and 2. The antibody or antigen-binding portion of the present invention can be used for therapeutic and diagnostic agents for use in targeting pathological condition associated with angiogenesis induced by angiopoietins. Therefore, the pharmaceutical compositions comprising the antibody or antigen-binding portion of the present invention can be used for diagnosing or treating patients with cancer, retinopathies, arthritis, psoriasis retinopathies, atherosclerosis, respiratory disease, obesity, diabetes, asthma, liver regeneration, pulmonary hypertension, or psoriasis.

Sequence Listing Free Text

SEQ ID NO: 1
Nucleotide sequence of heavy chain
variable region HC1
GAGGTGCAGCTGTTGGAGTCTGGGGGAGGCTTGGTACAGCCTGGGGGGT

CCCTGAGACTCTCCTGTGCAGCCTCTGGATTCACCTTTAGCGATTATTCT

ATGAGCTGGGTCCGCCAGGCTCCAGGGAAGGGGCTGGAGTGGGTCTCAGC

GATCTATCATAGTGGTAGTAATACATATTACGCTGATTCTGTAAAAGGTC

GGTTCACCATCTCCAGAGACAATTCCAAGAACACGCTGTATCTGCAAATG

AACAGCCTGAGAGCCGAGGACACGGCCGTGTATTACTGTGCGAGAGATGT

TGAGGCTAGGATGCTGCCTGCGTTCGACTACTGGGGCCAGGGTCCACTGG

TCACCGTCTCTAGT

SEQ ID NO: 2
Amino acid sequence of heavy chain
variable region HC1
EVQLLESGGGLVQPGGSLRLSCAASGFTFS<u>DYSMS</u>WVRQAPGKGLEWVS<u>A</u>

<u>IYHSGSNTYYADSVKGRFTISRDNSKNTLYLQMNSLRA</u><u>EDTAVYYCARDV</u>

<u>EARMLPAFDY</u>WGQGTLVTVSS

SEQ ID NO: 3
Nnucleotide sequence of heavy chain
variable region HC2
GAGGTGCAGCTGTTGGAGTCCGGGGGAGGCTTGGTACAGCCTGGGGGGT

CCCTGAGACTCTCCTGTGCAGCCTCTGGATTCACCTTTAGCAATTATGCT

ATGAGCTGGGTCCGCCAGGCTCCAGGGAAGGGGCTGGAGTGGGTCTCAGT

GATCTCTCCTGGTAGTGGTAATACATATTACGCTGATTCTGTAAAAGGTC

GGTTCACCATCTCCAGAGACAATTCCAAGAACACGCTGTATCTGCAAATG

AACAGCCTGAGAGCCGAGGACACGGCCGTGTATTACTGTGCGAAAGGTGC

TCTTAAGTGTAGGCATCGGTCGTGTTCTTCTTATAATGCTATGGACGTCT

GGGGCCAGGGTACACTGGTCACCGTCTCTAGT

SEQ ID NO: 4
Amino acid sequence of heavy chain
variable region HC2
EVQLLESGGGLVQPGGSLRLSCAASGFTFS<u>NYAMS</u>WVRQAPGKGLEWVS<u>V</u>

<u>ISPGSGNTYYADSVKGRFTISRDNSKNTLYLQMNSLRA</u><u>EDTAVYYCAKGA</u>

<u>LKCRHRSCSSYNAMDV</u>WGQGTLVTVSS

SEQ ID NO: 5
Nucleotide sequence of heavy chain
variable region HC3
GAGGTGCAGCTGTTGGAGTCTGGGGGAGGCTTGGTACAGCCTGGGGGGT

CCCTGAGACTCTCCTGTGCAGCCTCTGGATTCACCTTTAGCGATTATTAT

ATGAGCTGGGTCCGCCAGGCTCCAGGGAAGGGGCTGGAGTGGGTCTCATC

GATCTCTTATGATGATGGTAGTCGTAAATATTACGCTGATTCTGGTAAAA

GGTCGGTTACCATCTCCAGAGACAATTCCAAGAACACGCTGTATCTGCAA

ATGAACAGCCTGAGAGCCGAGGACACGGCCGTGTATTACTGTGCGAGAGA

TCGTTCTACTTTGCGTCTTGATAGTTTCGACTACTGGGGCCAGGGTACAC

TGGTCACCGTCTCTAGT

SEQ ID NO: 6
Amino acid sequence of heavy chain
variable region HC3
EVQLLESGGGLVQPGGSLRLSCAASGFTFS<u>DYYMS</u>WVRQAPGKGLEWVS<u>S</u>

<u>ISYDDGSRKYYADSGKR</u>SVTISRDNSKNTLYLQMNSLRA<u>EDTAVYYCARD</u>

<u>RSTLRLDSFDY</u>WGQGTLVTVSS

SEQ ID NO: 7
Nucleotide sequence of heavy chain
variable region HC4
GAGGTGCAGCTGTTGGAGTCCGGGGGAGGCCTGGTACAGCCTGGGGGGT

CCCTGAGACTCTCCTGTGCAGCCTCTGGATTCACCTTTAGCAATTATGCT

ATGAGCTGGGTCCGCCAGGCTCCAGGGAAGGGGCTGGAGTGGGTCTCAGC

GATCTCTCATGGTGGTAGTAGTAAATATTACGCTGATTCTGTAAAAGGTC

GGTTCACCATCTCCAGAGACAATTCCAAGAACACGCTGTATCTGCAAATG

AACAGCCTGAGAGCCGAGGACACGGCCGTGTATTACTGTGCGAGAGATCG

TACTGCGTCGCTTTTGGATGGTTTCGACTACTGGGGCCAGGGTACACTGG

TCACCGTCTCTAGT

SEQ ID NO: 8
Amino acid sequence of heavy chain
variable region HC4
EVQLLESGGGLVQPGGSLRLSCAASGFTFS<u>NYAMS</u>WVRQAPGKGLEWVSA <u>ISHGGSSKYYADSVKGR</u>FTISRDNSKNTLYLQMNSLRA<u>EDTAVYYCARDR</u>

<u>TASLLDGFDY</u>WGQGTLVTVSS

SEQ ID NO: 9
Nucleotide sequence of heavy chain
variable region HC5
GAGGTGCAGCTGTTGGAGTCTGGGGGAGGCTTGGTACAGACTGGGGGGT

CCCTGAGACTCTCCTGTGCAGCCTCTGGATTCACCTTTAGCGATTATGCT

ATGAGCTGGGTCCGCCAGGCTCCAGGGAAGGGGCTGGAGTGGGTCTCATC

GATCTCTTATGATGGTAGTAGTAAATATTACGCTGATTCTGTAAAAGGTC

GGTTCACCATCTCCAGAGACAATTCCAAGAACACGCTGTATCTGCAAATG

AACAGCCTGAGAGCCGAGGACACGGCCGTGTATTACTGTGCGAGACTTGC

TGGTGCTCGTGAGGATCATCCTGCGTCTTCTGATGATGCTATGGACGTCT

GGGGCCAGGGTACACTGGTCACCGTCTCTAGT

SEQ ID NO: 10
Amino acid sequence of heavy chain
variable region HC5
EVQLLESGGGLVQTGGSLRLSCAASGFTFS<u>DYAMS</u>WVRQAPGKGLEWVS<u>S</u>

<u>ISYDGSSKYYADSVKGR</u>FTISRDNSKNTLYLQMNSLRA<u>EDTAVYYCARLA</u>

<u>GAREDHPASSDDAMDV</u>WGQGTLVTVSS

SEQ ID NO: 11
Nucleotide sequence of heavy chain
variable region HC6
GAGGTGCAGCTGTTGGAGTCTGGGGGAGGCTTGGTACAGCCTGGGGGGT

CCCTGAGACTCTCCTGTGCAGCCTCTGGATTCACCTTTAGCAATTATTCT

ATGAGCTGGGTCCGCCAGGCTCCAGGGAAGGGGCTGGAGTGGGTCTCAGG

GATCTCTTCTGATGGTGGTAGTACATATTACGCTGATTCTGTAAGAGGTC

GGTTCACCATCTCCAGAGACAATTCCAAGAACACGCTGTATCTGCAAATG

AACAGCCTGGGAGCCGAGGACACGGCCGTGTATTACTGTGCGAGAGATGC

TCTTCAGCCTCGGAATAAGATGTGGTATTATTATTATGGTATGGACGTCT

GGGGCCAGGGTACACTGGTCACCGTCTCTAGT

SEQ ID NO: 12
Amino acid sequence of heavy chain
variable region HC6
EVQLLESGGGLVQPGGSLRLSCAASGFTFS<u>NYSMS</u>WVRQAPGKGLEWVSG <u>ISSDGGSTYYADSVRGR</u>FTISRDNSKNTLYLQMNSLGA<u>EDTAVYYCARDA</u>

<u>LQPRNKMWYYYYGMDV</u>WGQGTLVTVSS

SEQ ID NO: 13
Nucleotide sequence of heavy chain
variable region HC7
GAGGTGCAGCTGTTGGAGTCTGGGGGAGGCTTGGTACAGCCTGGGGGGT

CCCTGAGACTCTCCTGTGCAGCCTCTGGATTCACCTTTAGCGATCATGCT

ATGAGCTGGGTCCGCCAGGCTCCAGGGAAGGGGCTGGAGTGGGTCTCAGC

GATCTCTTCTGGTGGTAGTAGTACATATTACGCTGATTCTGTAAGAGGTC

GGTTCACCATCTCCAGAGACAATTCCAAGAACACGCTGTATCTGCAAATG

AACAGCCTGGGAGCCGAGGACACGGCCGTGTATTACTGTGCGAAATCTGG

TATTACGAAGGTGAGGAAGACGATGTCTTCTGCTTATGGTATGGACGTCT

GGGGCCAGGGTACACTGGTCACCGTCTCTAGT

SEQ ID NO: 14
Amino acid sequence of heavy chain
variable region HC7
EVQLLESGGGLVQPGGSLRLSCAASGFTFS<u>DHAMS</u>WVRQAPGKGLEWVSA <u>ISSGGSSTYYADSVRGR</u>FTISRDNSKNTLYLQMNSLGA<u>EDTAVYYCAKSG</u>

<u>ITKVRKTMSSAYGMDV</u>WGQGTLVTVSS

SEQ ID NO: 15
Nucleotide sequence of heavy chain
variable region HC8
GAGGTGCAGCTGTTGGAGTCTGGGGGAGGCTTGGTACAGCCTGGGGGGT

CCCTGAGACTCTCCTGTGCAGCCTCTGGATTCACCTTTAGCAATTATTCT

ATGAGCTGGGTCCGCCAGGCTCCAGGGAAGGGGCTGGAGTGGGTCTCAGC

GATCTCTCCTGGTAATGGTAATAAATATTACGCTGATTCTGTAAAAGGTC

GGTTCACCATCTCCAGAGACAATTCCAAGAACACGCTGTATCTGCAAATG

AACAGCCTGGGAGCCGAGGACACGGCCGTGTATTACTGTGCGAAAGGTCT

TAGTTCGCTTCTTCTGGTGGGGTTCGACTACTGGGGCCAGGGTACACTGG

TCACCGTCTCTAGT

SEQ ID NO: 16
Amino acid sequence of heavy chain
variable region HC8
EVQLLESGGGLVQPGGSLRLSCAASGFTFS<u>NYSMS</u>WVRQAPGKGLEWVSA <u>ISPGNGNKYYADSVKGR</u>FTISRDNSKNTLYLQMNSLRA<u>EDTAVYYCAKGL</u>

<u>SSLLLVGFDY</u>WGQGTLVTVSS

SEQ ID NO: 17
Nucleotide sequence of heavy chain
variable region HC9
GAGGTGCAGCTGTTGGAGTCTGGGGGAGGCTTGGTACAGCCTGGGGGGT

```
CCCTGAGACTCTCCTGTGCAGCCTCTGGATTCACCTTTAGCGATTATTCT

ATGAGCTGGGTCCGCCAGGCTCCAGGGAAGGGGCTGGAGTGGGTCTCAGC

GATCTATCCTAGTAGTAGTAATAAATATTACGCTGATTCTGTAAAAGGTC

GGTTCACCATCTCCAGAGACAATTCCAAGAACACGCTGTATCTGCAAATG

AACAGCCTGAGAGCCGAGGACACGGCCGTGTATTACTGTGCGAGAGATAC

TAGTCGGTGTGATAAGACTAAGTGTTATTATTATGATGCTATGGACGTCT

GGGGCCAGGGTACACTGGTCACCGTCTCTAGT
```

SEQ ID NO: 18
Amino acid sequence of heavy chain
variable region HC9
EVQLLESGGGLVQPGGSLRLSCAASGFTFS<u>DYSMS</u>WVRQAPGKGLEWVS<u>A IYPSSSNKYYADSVKG</u>RFTISRDNSKNTLYLQMNSLRA<u>EDTAVYYCARDT SRCDKTKCYYYDAMDV</u>WGQGTLVTVSS SEQ ID NO: 19
Nucleotide sequence of heavy chain
variable region HC10
```
GAGGTGCAGCTGGTGGAGTCTGGGGGAGGCTTGGTACAGCCTGGGGGGT

CCCTGAGACTCTCCTGTGCAGCCTCTGGATTCACCTTTAGCAATTATGCT

ATGAGCTGGGTCCGCCAGGCTCCAGGGAAGGGGCTGGAGTGGGTCTCATG

GATCTATCCTGATAATGGTAATACATATTACGCTGATTCTGTAAAAGGTC

GGTTCACCATCTCCAGAGACAATTCCAAGAACACGCTGTATCTGCAAATG

AACAGCCTGAGAGCCGAGGACACGGCCGTGTATTACTGTGCGAAATATAG

TCTTGATAAGTATACGCCGTGGCCGTATTCTTATTATGGTATGGACGTCT

GGGGCCAGGGTACACTGGTCACCGTCTCTAGT
```

SEQ ID NO: 20
Amino acid sequence of heavy chain
variable region HC10
EVQLVESGGGLVQPGGSLRLSCAASGFTFS<u>NYAMS</u>WVRQAPGKGLEWVS<u>W IYPDNGNTYYADSVKG</u>RFTISRDNSKNTLYLQMNSLRA<u>EDTAVYYCAKYS LDKYTPWPYSYYGMDV</u>WGQGTLVTVSS SEQ ID NO: 21
Nucleotide sequence of heavy chain
variable region HC11
```
GAGGTGCAGCTGTTGGAGTCTGGGGGAGGCTTGGTACAGCCTGGGGGGT

CCCTGAGACTCTCCTGTGCAGCCTCTGGATTCACCTTTAGCGATTATGCT

ATGAGCTGGGTCCGCCAGGCTCCAGGGAAGGGGCTGGAGTGGGTCTCAGC

GATCTCTTCTGATGGTGGTAGTACATATTACGCTGATTCTGTACAAGGTC

GGTTCACCATCTCCAGAGACAATTCCAAGAACACGCTGTATCTGCAAATG

AACAGCCTGAGAGCCGAGGACACGGCCGTGTATTACTGTGCGAGAGATCG

TTCGAAGTTGATGTTGCCTGGTTTCGACTACTGGGGCCAGGGTACACTGG

TCACCGTCTCTAGT
```

SEQ ID NO: 22
Amino acid sequence of heavy chain
variable region HC11
EVQLLESGGGLVQPGGSLRLSCAASGFTFS<u>DYAMS</u>WVRQAPGKGLEWVS<u>A ISSDGGSTYYADSVQG</u>RFTISRDNSKNTLYLQMNSLRA<u>EDTAVYYCARDR SKLMLPGFDY</u>WGQGTLVTVSS SEQ ID NO: 23
Nucleotide sequence of heavy chain
variable region HC12
```
GAGGTGCAGCTGTTGGAGTCCGGGGGAGGCTTGGTACAGCCTGGGGGGT

CCCTGAGACTCTCCTGTGCAGCCTCTGGATTCACCTTTAGCAATTATGCT

ATGAGCTGGGTCCGCCAGGCTCCAGGGAAGGGGCTGGAGTGGGTCTCAGT

GATCTCTCCTGGTAGTGGTAATACATATTACGCTGATTCTGTAAAAGGTC

GGTTCACCATCTCCAGAGACAATTCCAAGAACACGCTGTATCTGCAAATG

AACAGCCTGAGAGCCGAGGACACGGCCGTGTATTACTGTGCGAAAGGTGC

TCTTAAGTGTAGGCATCGGTCGTGTTCTTCTTATAATGCTATGGACGTCT

GGGGCCAGGGTACACTGGTCACCGTCTCTAGT
```

SEQ ID NO: 24
Amino acid sequence of heavy chain
variable region HC12
EVQLLESGGGLVQPGGSLRLSCAASGFTFS<u>NYAMS</u>WVRQAPGKGLEWVS<u>V ISPGSGNTYYADSVKG</u>RFTISRDNSKNTLYLQMNSLRA<u>EDTAVYYCAKGA LKCRHRSCSSYNAMDV</u>WGQGTLVTVSS SEQ ID NO: 25
Nucleotide sequence of heavy chain
variable region HC13
```
GAGGTGCAGCTGTTGGAGTCTGGGGGAGGCTTGGTACAGCCTGGGGGGT

CCCTGAGACTCTCCTGTGCAGCCTCTGGATTCACCTTTAGCAGTTATGAT

ATGAGCTGGGTCCGCCAGGCTCCAGGGAAGGGGCTGGAGTGGGTCTCATG

GATCCCTCCTGATAGTGGTAGTATATATTACGCTGATTCTGTAAAAGGTC

GGTTCACCATCTCCAGAGACAATTCCAAGAACACGCTGTATCTGCAAATG

AACAGCCTGAGAGCCGAGGACACGGCCGTGTATTACTGTGCGAGACATGC

TCCGGTTTTCGACTACTGGGGCCAGGGTACACTGGTCACCGTCTCTAGT
```

SEQ ID NO: 26
Amino acid sequence of heavy chain
variable region HC13
EVQLLESGGGLVQPGGSLRLSCAASGFTFS<u>SYDMS</u>WVRQAPGKGLEWVS<u>W IPPDSGSIYYADSVKG</u>RFTISRDNSKNTLYLQMNSLRA<u>EDTAVYYCARHA PVFDY</u>WGQGTLVTVSS SEQ ID NO: 27
Nucleotide sequence of heavy chain
variable region HC14
```
GAGGTGCAGCTGTTGGAGTCTGGGGGAGGCTTGGTACAGCCTGGGGGGT

CCCTGGGACTCTCCTGTGCAGCCTCTGGATTCACCCTTAGCAATTATGAT

ATGAGCTGGGTCCGCCAGGCTCCAGGGAAGGGGCTGGAGTGGGTCTCATG

GATCTCTCCTGATAGTAGTAGTACATATTACGCTGATTCTGTAAAAGGTC

GGTTCACCATCTCCAGAGACAATTCCAAGAACACGCTGTATCTGCAAATG

AACAGCCTGAGAGCCGAGGACACGGCCGTGTATTACTGTGCGAGATCTGT

TATGCCTTTCGACTACTGGGGCCAGGGTACACTGGTCACCGTCTCTAGT
```

SEQ ID NO: 28
Amino acid sequence of heavy chain
variable region HC14
EVQLLESGGGLVQPGGSLGLSCAASGFTLS<u>NYDMS</u>WVRQAPGKGLEWVS<u>W ISPDSSSTYYADSVKG</u>RFTISRDNSKNTLYLQMNSLRA<u>EDTAVYYCARSV MPFDY</u>WGQGTLVTVSS SEQ ID NO: 29
Nucleotide sequence of heavy chain
variable region HC15
GAGGTGCAGCTGTTGGAGTCTGGGGGAGGCTTGGTACAGCCTGGGGGT
CCCTGAGACTCTCCTGTGCAGCCTCTGGATTCACCTTTAGCGATTATGAT
ATGAGCTGGGTCCGCCAGGCTCCAGGGGAGGGGCTGGAGTGGGTCTCATG
GATCTCTCCTGATAGTGGTAGTATATATTACGCTGATTCTGTAAAAGGTC
GGTTCACCATCTCCAGAGACAATTCCAAGAACACGCTGTATCTGCAAATG
AACAGCCTGAGAGCCGAGGACGCGGCCGTGTATTACTGTGCGAGACTTGC
TCCTGAGTTCGACTACTGGGGCCAGGGTACACTGGTCACCGTCTCTAGT SEQ ID NO: 30
Amino acid sequence of heavy chain
variable region HC15
EVQLLESGGGLVQPGGSLRLSCAASGFTFS<u>DYDMS</u>WVRQAPGEGLEWVS<u>W
ISPDSGSIYYADSVKG</u>RFTISRDNSKNTLYLQMNSLRAE<u>DAAVYYCARLA
PEFDY</u>WGQGTLVTVSS SEQ ID NO: 31
Nucleotide sequence of heavy chain
variable region HC16
GAGGTGCAGCTGTTGGAGTCTGGGGGAGGCTTGGTACAGCCTGGGGGT
CCCTGAGACTCTCCTGTGCAGCCTCTGGATTCACCTTTAGCGATTATTAT
ATGAGCTGGGTCCGCCAGGCTCCAGGGGAAGGGGCTGGAGTGGGTCTCATC
GATCTCTTATGATGATGGTAGTCGTAAATATTACGCTGATTCTGGTAAAA
GGTCGGTTACCATCTCCAGAGACAATTCCAAGAACACGCTGTATCTGCAA
ATGAACAGCCTGAGAGCCGAGGACACGGCCGTGTATTACTGTGCGAGAGA
TCGTTCTACTTTGCGTCTTGATAGTTTCGACTACTGGGGCCAGGGTACAC
TGGTCACCGTCTCTAGT SEQ ID NO: 32
Amino acid sequence of heavy chain
variable region HC16
EVQLLESGGGLVQPGGSLRLSCAASGFTFS<u>DYYMS</u>WVRQAPGKGLEWVS<u>S
ISYDDGSRKYYADSGKR</u>SVTISRDNSKNTLYLQMNSLRAE<u>DTAVYYCARD
RSTLRLDSFDY</u>WGQGTLVTVSS SEQ ID NO: 33
Nucleotide sequence of heavy chain
variable region HC17
GAGGTGCAGCTGTTGGAGTCTGGGGGAGGCTTGGTACAGCCTGGGGGT
CCCTGAGACTCTCCTGTGCAGCCTCTGGATTCACCTTTAGCAGTTATTCT
ATGAGCTGGGTCCGCCAGGCTCCAGGGGAAGGGGCTGGAGTGGGTCTCAGC
GATCTCTCCTGGTAGTAGTAATAAATATTACGCTGATTCTGTAAAAGGTC
GGTTCACCATCTCCAGAGACAATTCCAAGAACACGCTGTATCTGCAAATG
AACAGCCTGAGAGCCGAGGACACGGCCGTGTATTACTGTGCGAGAGGTGT
TAGTCGTTCGCGGCATTATCCTACGTATTATTATAATGGTATGGACGTCT
GGGGCCAGGGTACACTGGTCACCGTCTCTAGT SEQ ID NO: 34
Amino acid sequence of heavy chain
variable region HC17
EVQLLESGGGLVQPGGSLRLSCAASGFTFS<u>SYSMS</u>WVRQAPGKGLEWVS<u>A
ISPGSSNKYYADSVKG</u>RFTISRDNSKNTLYLQMNSLRAE<u>DTAVYYCARGV
SRSRHYPTYYYNGMDV</u>WGQGTLVTVSS SEQ ID NO: 35
Nucleotide sequence of heavy chain
variable region HC18
GAGGTGCAGCTGTTGGAGTCTGGGGGAGGCTTGGTACAGCCTGGGGGT
CCCTGAGACTCTCCTGTGCAGCCTCTGGATTCACCTTTAGCGATTATGAT
ATGAGCTGGGTCCGCCAGGCTCCAGGGAAGGGGCTGGAGTGGGTCTCATG
GATCTCTCCTGATGATGGTAGTATATATTACGCTGATTCTGTAAAAGGTC
GGTTCACCATCTCCAGAGACAATTCCAAGAACACGCTGTATCTGCAAATG
AACAGCCTGAGAGCCGAGGACACGGCCGTGTATTACTGTGCGAGATCTGT
GCTGCCGTTCGACTACTGGGGCCAGGGTACACTGGTCACCGTCTCTAGT SEQ ID NO: 36
Amino acid sequence of heavy chain
variable region HC18
EVQLLESGGGLVQPGGSLRLSCAASGFTFS<u>DYDMS</u>WVRQAPGKGLEWVS<u>W
ISPDDGSIYYADSVKG</u>RFTISRDNSKNTLYLQMNSLRAE<u>DTAVYYCARSV
LPFDY</u>WGQGTLVTVSS SEQ ID NO: 37
Nucleotide of heavy chain variable
region HC19
GAGGTGCAGCTGGTACAGTCTGGGGGAGGTGTGGTCCAGCCTGGGAGGT
CCCTGAGACTCTCCTGTGCAGCGTCTGGATTCACCTTCAGTAAATATGGC
ATGCACTGGGTCCGCCAGGCTCCAGGCAAGGGGCTGGAATGGCTGGCATT
TATTTGGTTTGATGGAAGTAATAAATTCTATGCAGACTCCGTGAAGGGCC
GATTCACCGTCTCCAGAGACAATTCCAAGAACACCCTGTTTCTGCAAATG
AACAGCCTGAGAGCCGAGGACACGGCCGTGTATTACTGTGCGAGAGGCCA
TAAGTTTGGTGACTACGACGGGGTGGACCGGTTCGACCCCTGGGGCCAGG
GAACCCTGGTCACCGTCTCTAGT SEQ ID NO: 38
Amino acid sequence of heavy chain
variable region HC19
EVQLVQSGGGVVQPGRSLRLSCAASGFTFS<u>KYGMH</u>WVRQAPGKGLEWLA<u>F
IWFDGSNKFYADSVKG</u>RFTVSRDNSKNTLFLQMNSLRAE<u>DTAVYYCARGH
KFGDYDGVDRFDP</u>WGQGTLVTVSS SEQ ID NO: 39
Nucleotide sequence of heavy chain
variable region HC20
GAGGTGCAGCTGGTGGAGTCTGGGGGAGGCTTGGTACAGCCTGGGGGT
CCCTGAGACTCTCCTGTGCAGCCTCTGGATTCACCTTTAGCAGCTATGCC
ATGAGCTGGGTCCGCCAGGCTCCAGGGAAGGGGCTGGAGTGGGTCTCAGC
TATTAGTGGTAGTGGTGGTAGCACATTCTACGCAGACTCCGTGAAGGGCC
GGTTCACCATCTCCAGAGACAATTCCAAGAACACGGTGTATCTGCAAATG
AACAGTCTGAGAGCCGAGGACACGGCCGTGTATTACTGTGCGAGAGGGGG
CGACTACGGTTCGGGGACTTATTATGACCTCTGGGGCCGCGGAACCCTGA
TCACCGTCTCTAGT SEQ ID NO: 40
Amino acid sequence of heavy chain
variable region HC20
EVQLVESGGGLVQPGGSLRLSCAASGFTFS<u>SYAMS</u>WVRQAPGKGLEWVS<u>A
ISGSGGSTFYADSVKG</u>RFTISRDNSKNTVYLQMNSLRAE<u>DTAVYYCARGG
DYGSGTYYDL</u>WGRGTLITVSS SEQ ID NO: 41
Nucleotide sequence of heavy chain
variable region HC21
GAGGTGCAGCTGGTAGAGTCGGGGGGAGGCGTGGTTCAGCCTGGGGGT

CCCTGAGACTCTCCTGTGTAGCCTCTGGATTCACTTTTAATGAACACGCC

ATGCACTGGGTCCGTCAAGCTCCAGGAAAGGGTCTGGAGTGGATCGCTCT

TATTGGTGCGGATGGTGTCACTACTTACTCTGCAGACTCTGTGGAGGGCC

GAATCACCATCTCCCGAGACAACAGCAAAAACTCCCTGTATCTGCAAATG

AACAGTCTGAGAGCCGAGGACACGGCCGTGTATTACTGTGCGAGAGGGTC

TCGCTTTGATACGAGTGGTCCCATTGATCATTGGGGCCAGGGAACCCCGG

TCACCGTCTCTAGT

SEQ ID NO: 42
Amino acid sequence of heavy chain
variable region HC21
EVQLVESGGGVVQPGGSLRLSCVASGFTFNEHAMHWVRQAPGKGLEWIAL

IGADGVTTYSADSVEGRITISRDNSKNSLYLQMNSLRAEDTAVYYCARGS

RFDTSGPIDHWGQGTPVTVSS

SEQ ID NO: 43
Nucleotide sequence of heavy chain
variable region HC22
GAGGTGCAGCTGGTACAGTCTGGGGCTGAGGTGAAGAAGCCTGGGGCCT

CAGTGAAGGTTTCCTGCAAGGCTTCTGGAGGCACCTTCAGCAGCTATGCT

ATCAGCTGGGTGCGACAGGCCCCTGGACAAGGGCTTGAGTGGATGGGAGG

GATCATCCCTATCTTTGGTACAGCAAACTACGCACAGAAGTTCCAGGGCA

GAGTCACGATTACCGCGGACGAATCCACGAGCACAGCCTACATGGAGCTG

AGCAGCCTGAGATCTGAGGACACGGCCGTGTATTACTGTGCGAGAGGCGG

TTCGGGGAGGTTTGACTACTGGGGCCAGGGAACCCTGGTCACCGTCTCTA

GT

SEQ ID NO: 44
Amino acid sequence of heavy chain
variable region HC22
EVQLVQSGAEVKKPGASVKVSCKASGGTFSSYAISWVRQAPGQGLEWMGG

IIPIFGTANYAQKFQGRVTITADESTSTAYMELSSLRSEDTAVYYCARGG

SGRFDYWGQGTLVTVSS

SEQ ID NO: 45
Nucleotide sequence of light chain
variable region LC1
CAGTCTGTGCTGACTCAGCCACCCTCAGCGTCTGGGACCCCCGGGCAGAG

GGTCACCATCTCTTGTAGTGGCTCTTCATCTAATATTGGCAATAATGATG

TCTCCTGGTACCAGCAGCTCCCAGGAACGGCCCCCAAACTCCTCATCTAT

TCTGATAGTCAGCGGCCAAGCGGGGTCCCTGACCGATTCTCTGGCTCCAA

GTCTGGCACCTCAGCCTCCCTGGCCATCAGTGGGCTCCGGTCCGAGGATG

AGGCTGATTATTACTGTGGTTCTTGGGATGCTAGCCTGAATGGTTATGTC

TTCGGCGGAGGCACCAAGCTGACGGTCCTA

SEQ ID NO: 46
Amino acid sequence of light chain
variable region LC1
QSVLTQPPSASGTPGQRVTISCSGSSSNIGNNDVSWYQQLPGTAPKLLIY

SDSQRPSGVPDRFSGSKSGTSASLAISGLRSEDEADYYCGSWDASLNGYV

FGGGTKLTVL

SEQ ID NO: 47
Nucleotide sequence of light chain
variable region LC2
CAGTCTGTGCTGACTCAGCCACCCTCAGCGTCTGGGACCCCCGGGCAGAG

GGTCACCATCTCTTGTACTGGCTCTTCATCTAATATTGGCAATAATGATG

TCTCCTGGTACCAGCAGCTCCCAGGAACGGCCCCCAAACTCCTCATCTAT

GATAATAATCATCGGCCAAGCGGGGTCCCTGACCGATTCTCTGGCTCCAA

GTCTGGCACCTCAGCCTCCCTGGCCATCAGTGGGCTCCGGTCCGAGGATG

AGGCTGATTATTACTGTGGTACTTGGGATGCTAGCCTGAATGGTTATGTC

TTCGGCGGAGGCACCAAGCTGACGGTCCTA

SEQ ID NO: 48
Amino acid sequence of light chain
variable region LC2
QSVLTQPPSASGTPGQRVTISCTGSSSNIGNNDVSWYQQLPGTAPKLLIY

DNNHRPSGVPDRFSGSKSGTSASLAISGLRSEDEADYYCGTWDASLNGYV

FGGGTKLTVL

SEQ ID NO: 49
Nucleotide sequence of light chain
variable region LC3
CAGTCTGTGCTGACTCAGCCACCCTCAGCGTCTGGGACCCCCGGGCGGAG

GGTCACCATCTCTTGTAGTGGCTCTTCACCTAATATTGGCAATAATACTG

TCAACTGGTACCAGCAGCTCCCAGGAACGGCCCCCAAACTCCTCATCTAT

TCTGATAGTCATCGGCCAAGCGGGGTCCCTGACCGATTCTCTGGCTCCAA

GTCTGGCACCTCAGCCTCCCTGGCCATCAGTGGGCTCCGGTCCGAGGATG

AGGCTGATTATTACTGTGGTGCTTGGGATTATAGCCTGAATGCTTATGTC

TTCGGCGGAGGCACCAAGCTGACGGTCCTA

SEQ ID NO: 50
Amino acid sequence of light chain
variable region LC3
QSVLTQPPSASGTPGRRVTISCSGSSPNIGNNTVNWYQQLPGTAPKLLIY

SDSHRPSGVPDRFSGSKSGTSASLAISGLRSEDEADYYCGAWDYSLNAYV

FGGGTKLTVL

SEQ ID NO: 51
Nucleotide sequence of light chain
variable region LC4
CAGTCTGTGCTGACTCAGCCACCCTCAGCGTCTGGGACCCCCGGGCAGAG

GGTCACCATCTCTTGTAGTGGCTCTTCATCTAATATTGGCAATAATTATG

TCAACTGGTACCAGCAGCTCCCAGGAACGGCCCCCAAACTCCTCATCTAT

GCTGATAGTAATCGGCCAAGCGGGGTCCCTGACCGATTCTCTGGCTCCAA

GTCTGGCACCTCAGCCTCCCTGGCCATCAGTGGGCTCCGGTCCGAGGATG

AGGCTGATTATTACTGTGGTACTTGGGATGCTAGCCTGAGTGGTTATGTC

TTCGGCGGAGGCACCAAGCTGACGGTCCTA

SEQ ID NO: 52
Amino acid sequence of light chain
variable region LC4
QSVLTQPPSASGTPGQRVTISCSGSSSNIGNNYVNWYQQLPGTAPKLLIY

ADSNRPSGVPDRFSGSKSGTSASLAISGLRSEDEADYYCGTWDASLSGYV

FGGGTKLTVL

SEQ ID NO: 53
Nucleotide sequence of light chain
variable region LC5
CAGTCTGTGCTGACTCAGCCACCCTCAGCGTCTGGGACCCCCGGGCAGAG

GGTCACCATCTCTTGTAGCGGCGATAGCATTCCTTCTAAATATGCGTATT

-continued
GGTACCAGCAGCTCCCAGGAACGGCCCCCAAACTCCTCATCTATTCTAAT

AATCAGCGGCCAAGCGGGGTCCCTGACCGATTCTCTGGCTCCAAGTCTGG

CACCTCAGCCTCCCTGGCCATCAGTGGGCTCCGGTCCGAGGATGAGGCTG

ATTATTACTGTGGTTCTTGGGATTCTAGCCTGAGTGCTTATGTCTTCGGC

GGAGGCACCAAGCTGACGGTCCTA

SEQ ID NO: 54
Amino acid sequence of light chain
variable region LC5
QSVLTQPPSASGTPGQRVTISC<u>SGDSIPSKYAY</u>WYQQLPGTAPKLLIY<u>SN</u>

<u>NQRPS</u>GVPDRFSGSKSGTSASLAISGLRSEDEADYYC<u>GSWDSSLSAYV</u>FG

GGTKLTVL

SEQ ID NO: 55
Nucleotide sequence of light chain
variable region LC6
CAGTCTGTGCTGACTCAGCCACCCTCAGCGTCTGGGACCCCCGGGCAGAG

GGTCACCATCTCTTGTAGTGGCTCTTCATCTAATATTGGCAGTAATGCTG

TCAACTGGTACCAGCAGCTCCCAGGAACGGCCCCCAAACTCCTCATCTAT

GCTGATAGTAATCGGCCAAGCGGGTCCCTGACCGATTCTCTGGCTCCAA

GTCTGGCACCTCAGCCTCCCTGGCCATCAGTGGGCTCCGGTCCGAGGATG

AGGCTGATTATTACTGTGGTTCTTGGGATTATAGCCTGAGTGGTTATGTC

TTCGGCGGAGGCACCAAGCTGACGGTCCTA

SEQ ID NO: 56
Amino acid sequence of light chain
variable region LC6
QSVLTQPPSASGTPGQRVTISC<u>SGSSSNIGSNAVN</u>WYQQLPGTAPKLLIY <u>ADSNRPS</u>GVPDRFSGSKSGTSASLAISGLRSEDEADYYC<u>GSWDYSLSGYV</u>

FGGGTKLTVL

SEQ ID NO: 57
Nucleotide sequence of light chain
variable region LC7
CAGTCTGTGCTGACTCAGCCACCCTCAGCGTCTGGGACCCCCGGGCAGAG

GGTCACCATCTCTTGTAGTGGCTCTTCATCTAATATTGGCAATAATTCTG

TCTACTGGTACCAGCAGCTCCCAGGAACGGCCCCCAAACTCCTCATCTAT

GCTAATAGTCATCGGCCAAGCGGGTCCCTGACCGATTCTCTGGCTCCAA

GTCTGGCACCTCAGCCTCCCTGGCCATCAGTGGGCTCCGGTCCGAGGATG

AGGCTGATTATTACTGTGGTACTTGGGATTATAGCCTGAGTGGTTATGTC

TTAGGCGGAGGCACCAAGCTGACGGTCCTA

SEQ ID NO: 58
Amino acid sequence of light chain
variable region LC7
QSVLTQPPSASGTPGQRVTISC<u>SGSSSNIGNNSVY</u>WYQQLPGTAPKLLIY <u>ANSHRPS</u>GVPDRFSGSKSGTSASLAISGLRSEDEADYYC<u>GTWDYSLSGYV</u>

LGGGTKLTVL

SEQ ID NO: 59
Nucleotide sequence of light chain
variable region LC8
CAGTCTGTGCTGACTCAGCCACCCTCAGCGTCTGGGACCCCCGGGCAGAG

GGTCACCATCTCTTGTAGTGGCTCTTCATCTAATATTGGCAATAATGATG

TCTCCTGGTACCAGCAGCTCCCAGGAACGGCCCCCAAACTCCTCATCTAT

TCTGATAGTCAGCGGCCAAGCGGGGTCCCCGACCGATTCTCTGGCTCCAA

GTCTGGCACCTCAGCCTCCCTGGCCATCAGTGGGCTCCGGTCCGAGGATG

AGGCTGATTATTACTGTGGTTCTTGGGATGCTAGCCTGAATGGTTATGTC

TTCGGCGGAGGCACCAAGCTGACGGTCCTA

SEQ ID NO: 60
Amino acid sequence of light chain
variable region LC8
QSVLTQPPSASGTPGQRVTISC<u>SGSSSNIGNNDVS</u>WYQQLPGTAPKLLIY <u>SDSQRPS</u>GVPDRFSGSKSGTSASLAISGLRSEDEADYYC<u>GSWDASLNGYV</u>

FGGGTKLTVL

SEQ ID NO: 61
Nucleotide sequence of light chain
variable region LC9
294CAGTCTGTGCTGACTCAGCCACCCTCAGCGTCTGGGACCCCCGGGCA

GAGGGTCACCATCTCTTGTACTGGCTCTTCATCTAATATTGGCAATAATG

CTGTCTCCTGGTACCAGCAGCTCCCAGGAACGGCCCCCAAACTCCTCATC

TATGATGATAATCATCGGCCAAGCGGGGTCCCTGACCGATTCTCTGGCTC

CAAGTCTGGCACCTCAGCCTCCCTGGCCATCAGTGGGCTCCGGTCCGAGG

ATGAGGCTGATTATTACTGTGGTTCTTGGGATGCTAGCCTGAATGGTTAT

GTCTTCGGCGGAGGCACCAAGCTGACGGTCCTA

SEQ ID NO: 62
Amino acid sequence of light chain
variable region LC9
QSVLTQPPSASGTPGQRVTISC<u>TGSSSNIGNNAVS</u>WYQQLPGTAPKLLIY <u>DDNHRPS</u>GVPDRFSGSKSGTSASLAISGLRSEDEADYYC<u>GSWDASLNGYV</u>

FGGGTKLTVL

SEQ ID NO: 63
Nucleotide sequence of light chain
variable region LC10
CAGTCTGTGCTGACTCAGCCACCCTCAGCGTCTGGGACCCCCGGGCAGAG

GGTCACCATCTCTTGTACTGGCTCTTCATCTAATATTGGCAATAATGCTG

TCACCTGGTACCAGCAGCTCCCAGGAACGGCCCCCAAACTCCTCATCTAT

GATGATAGTCATCGGCCAAGCGGGGCCCCTGACCGATTCTCTGGCTCCAA

GTCTGGCACCTCAGCCTCCCTGGCCATCAGTGGGCTCCGGTCCGAGGATG

AGGCTGATTATTACTGTGGTACTTGGGATGCTAGCCTGAGTGCTTATGTC

TTCGGCGGAGGCACCAAGCTGACGGTCCTA

SEQ ID NO: 64
Amino acid sequence of light chain
variable region LC10
QSVLTQPPSASGTPGQRVTISC<u>TGSSSNIGNNAVT</u>WYQQLPGTAPKLLIY <u>DDSHRPS</u>GAPDRFSGSKSGTSASLAISGLRSEDEADYYC<u>GTWDASLSAYV</u>

FGGGTKLTVL

SEQ ID NO: 65
Nucleotide sequence of light chain
variable region LC11
CAGTCTGTGCTGACTCAGCCACCCTCAGCGTCTGGGACCCCCGGGCAGAG

GGTCACCATCTCTTGTGGCGGCGATAACATTCCTTATAAATATGCGGATT

GGTACCAGCAGCTCCCAGGAACGGCCCCCAAACTCCTCATCTATTCTGAT

AATAAGCGGCCAAGCGGGGTCCCTGACCGATTCTCTGGCTCCAAGTCTGG

CACCTCAGCCTCCCTGGCCATCAGTGGGCTCCGGTCCGAGGATGAGGCTG

ATTATTACTGTGCTTCTTGGGATGCTAGCCTGAATGGTTATGTCTTCGGC

GGAGGCACCAAGCTGACGGTCCTA

SEQ ID NO: 66
Amino acid sequence of light chain
variable region LC11
QSVLTQPPSASGTPGQRVTISC<u>GGDNIPYKYAD</u>WYQQLPGTAPKLLIY<u>SD</u>

<u>NKRPS</u>GVPDRFSGSKSGTSASLAISGLRSEDEADYYC<u>ASWDASLNGYV</u>FG

GGTKLTVL

SEQ ID NO: 67
Nucleotide sequence of light chain
variable region LC12
CAGTCTGTGCTGACTCAGCCACCCTCAGCGTCTGGGACCCCCGGGCAGAG

GGTCACCATCTCTTGTACTGGCTCTTCATCTAATATTGGCAATAATGATG

TCTCCTGGTACCAGCAGCTCCCAGGAACGGCCCCCAAACTCCTCATCTAT

GATAATAATCATCGGCCAAGCGGGTCCCTGACCGATTCTCTGGCTCCAA

GTCTGGCACCTCAGCCTCCCTGGCCATCAGTGGGCTCCGGTCCGAGGATG

AGGCTGATTATTACTGTGGTACTTGGGATGCTAGCCTGAATGGTTATGTC

TTCGGCGGAGGCACCAAGCTGACGGTCCTA

SEQ ID NO: 68
Amino acid sequence of light chain
variable region LC12
QSVLTQPPSASGTPGQRVTISC<u>TGSSSNIGNNDVS</u>WYQQLPGTAPKLLIY <u>DNNHRPS</u>GVPDRFSGSKSGTSASLAISGLRSEDEADYYC<u>GTWDASLNGYV</u>

FGGGTKLTVL

SEQ ID NO: 69
Nucleotide sequence of light chain
variable region LC13
CAGTCTGTGCTGACTCAGCCACCCTCAGCGTCTGGGACCCCCGGGCAGGG

GGTCACCATCTCTTGTACTGGCTCTTCATCTAATATTGGCAATAATAATG

TCTACTGGTACCAGCAGCTCCCAGGAACGGCCCCCAAACTCCTCATCTAT

TCTGATAATAATCGGCCAAGCGGGTCCCTGACCGATTCTCTGGCTCCAA

GTCTGGCACCTCAGCCTCCCTGGCCATCAGTGGGCTCCGGTCCGAGGATG

AGGCTGATTATTACTGTGGTGCTTGGGATGATAGCCTGAGTGCTTATGTC

TTCGGCGGAGGCACCAAGCTGACGGTCCTA

SEQ ID NO: 70
Amino acid sequence of light chain
variable region LC13
QSVLTQPPSASGTPGQGVTISC<u>TGSSSNIGNNNVY</u>WYQQLPGTAPKLLIY <u>SDNNRPS</u>GVPDRFSGSKSGTSASLAISGLRSEDEADYYC<u>GAWDDSLSAYV</u>

FGGGTKLTVL

SEQ ID NO: 71
Nucleotide sequence of light chain
variable region LC14
CAGTCTGTGCTGACTCAGCCACCCTCAGCGTCTGGGACCCCCGGGCAGAG

GGTCACCATCTCTTGTAGTGGCTCTTCATCTAATATTGGCAGTAATGCTG

TCTACTGGTACCAGCAGCTCCCAGGAACGGCCCCCAAACTCCTCATCTAT

GATGATAGTAAGCGGCCAAGCGGGTCCCTGACCGATTCTCTGGCTCCAA

GTCTGGCACCTCAGCCTCCCTGGCCATCGGTGGGCTCCGGTCCGAGGATG

AGGCTGATTATTACTGTGGTGCTTGGGATGATAGCCTGAGTGCTTATGTC

TTCGGCGGAGGCACCAAGCTGACGGTCCTA

SEQ ID NO: 72
Amino acid sequence of light chain
variable region LC14
QSVLTQPPSASGTPGQRVTISC<u>SGSSSNIGSNAVY</u>WYQQLPGTAPKLLIY <u>DDSKRPS</u>GVPDRFSGSKSGTSASLAIGGLRSEDEADYYC<u>GAWDDSLSAYV</u>

FGGGTKLTVL

SEQ ID NO: 73
Nucleotide sequence of light chain
variable region LC15
CAGTCTGTGCTGACTCAGCCACCCTTCAGCGTCTGGGACCCCCGGGCAGAG

GGTCACCATCTCTTGTAGTGGCTCTTCATCTAATATTGGCAGTAATACTG

TCTACTGGTACCAGCAGCTCCCAGGAACGGCCCCCAAACTCCTCATCTAT

GATGATAATCATCGGCCAAGCGGGTCCCTGACCGATTCTCTGGCTCCAA

GTCTGGCACCTCAGCCTCCCTGGCCATCAGTGGGCTCCGGTCCGAGGATG

AGGCTGATTATTACTGTGGTGCTTGGGATGATAGCCTGAGTGCTTATGTC

TTCGGCGGAGGCACCAAGCTGACGGTCCTA

SEQ ID NO: 74
Amino acid sequence of light chain
variable region LC15
QSVLTQPPSASGTPGQRVTISC<u>SGSSSNIGSNTVY</u>WYQQLPGTAPKLLIY <u>DDNHRPS</u>GVPDRFSGSKSGTSASLAISGLRSEDEADYYC<u>GAWDDSLSAYV</u>

FGGGTKLTVL

SEQ ID NO: 75
Nucleotide sequence of light chain
variable region LC16
336CAGTCTGTGCTGACTCAGCCACCCTCAGCGTCTGGGACCCCCGGGCG

GAGGGTCACCATCTCTTGTAGTGGCTCTTCACCTAATATTGGCAATAATA

CTGTCAACTGGTACCAGCAGCTCCCAGGAACGGCCCCCAAACTCCTCATC

TATTCTGATAGTCATCGGCCAAGCGGGGTCCCTGACCGATTCTCTGGCTC

CAAGTCTGGCACCTCAGCCTCCCTGGCCATCAGTGGGCTCCGGTCCGAGG

ATGAGGCTGATTATTACTGTGGTGCTTGGGATTATAGCCTGAATGCTTAT

GTCTTCGGCGGAGGCACCAAGCTGACGGTCCTA

SEQ ID NO: 76
Amino acid sequence of light chain
variable region LC16
QSVLTQPPSASGTPGRRVTISC<u>GSSPNIGNNTVN</u>WYQQLPGTAPKLLIY <u>SDSHRPS</u>GVPDRFSGSKSGTSASLAIGLRSEDEADYYC<u>GAWDYSLNAYV</u>

FGGGTKLTVL

SEQ ID NO: 77
Nucleotide sequence of light chain
variable region LC17
CAGTCTGTGCTGACTCAGCCACCCTCAGCGCCTGGGACCCCCGGGCAGAG

GGTCACCATCTCTTGTAGTGGCTCTTCATCTAATATTGGCAGTAATGCTG

TCACCTGGTACCAGCAGCTCCCAGGAACGGCCCCCAAACTCCTCATCTAT

TATGATAATAATCGGCCAAGCGGGTCCCTGACCGATTCTCTGGCTCCAA

GTCTGGCACCTCAGCCTCCCTGGCCATCAGTGGGCTCCGGTCCGAGGATG

AGGCTGATTATTACTGTGGTACTTGGGATTATAGCCTGAGTGGTTATGTC

TTAGGCGGAGGCACCAAGCTGACGGTCCTA

SEQ ID NO: 78
Amino acid sequence of light chain
variable region LC17
QSVLTQPPSAPGTPGQRVTISC<u>SGSSSNIGSNAVT</u>WYQQLPGTAPKLLIY <u>YDNNRPS</u>GVPDRFGSKSGTSASLAISGLRSEDEADYYC<u>GTWDYSLSGYV</u>

LGGGTKLTVL

SEQ ID NO: 79
Nucleotide sequence of light chain
variable region LC18
CAGTCTGTGCTGACTCAGCCACCCTCAGCGTCTGGGACCCCCGGGCAGAG

GGTCACCATCTCTTGTAGTGGCTCTTCATCTAATATTGGCAGTAATGCTG

TCTACTGGTACCAGCAGCTCCCAGGAACGGCCCCCAAACTCCTCATCTAT

GATGATAGTAAGCGGCCAAGCGGGGTCCCTGACCGATTCTCTGGCTCCAA

GTCTGGCACCTCAGCCTCCCTGGCCATCAGTGGGTTCCGGTCCGAGGATG

AGGCTGATTATTACTGTGGTTCTTGGGATGCTAGCCTGAATGCTTATGTC

TTCGGCGGAGGCACCAAGCTGACGGTCCTA

SEQ ID NO: 80
Amino acid sequence of light chain
variable region LC18
QSVLTQPPSASGTPGQRVTISC<u>SGSSSNIGSNAVY</u>WYQQLPGTAPKLLIY <u>DDSKRPS</u>GVPDRFGSKSGTSASLAISGFRSEDEADYYC<u>GSWDASLNAYV</u>

FGGGTKLTVL

SEQ ID NO: 81
Nucleotide sequence of light chain
variable region LC19
GATATTGTGATGACCCAGACTCCACTCTCCCTGCCCGTCACCCCTGGACA

GCCGGCCTCCATCTCCTGCAGGTCTAGTCAGAGCCTCTTCGATAGTGATG

ATGGCAACACCTATTTGGACTGGTACCTGCAGAAGCCAGGGCAGTCTCCA

CAGCTCCTGATCTATGCGCTTTCCTATCGGGCCTCTGGAGTCCCAGACAG

GTTCAGTGGCAGTGGGTCAGGCACTGATTTCACACTGAAAATCAGCAGGG

TGGAGGCTGAGATTCTGGAATATATTACTGCATGCAACGTGTGGAGTTT

CCTTATACTTTTGGCCAGGGGACCAAGCTGGAAATCAAACGT

SEQ ID NO: 82
Amino acid sequence of light chain
variable region LC19
DIVMTQTPLSLPVTPGQPASISC<u>RSSQSLFDSDDGNTYLD</u>WYLQKPGQSP QLLIY<u>ALSYRAS</u>GVPDRFGSGSGTDFTLKISRVEAGDSGIYYC<u>MQRVEF</u>

<u>PYT</u>FGQGTKLEIKR

SEQ ID NO: 83
Nucleotide sequence of light chain
variable region LC20
TCCTATGAGCTGACTCAGCCACCCTCAGTGTCAGTGGCCCCAGGCAGGAC

GGCCACACTTACCTGTGGGGGAGATAACATTGAACATAAAAGTGTGCACT

GGTACCAGCAGAAGCCAGGCCAGGCCCCTTTGTTGATCATGTATTACGAT

AGTGACCGGCCCTCAGGGGTCCCGGAGCGATTCTCTGGCTCCAACTTTGG

AAACACGGCCACCCTGACCATCGACAGGGTCGAAGCCGGGGATGAGGCCG

ACTATTATTGTCAAGTGTGGGATAATTTTACTGAACATCCGGTGTTCGGC

AGAGGGACCAAGCTGACCGTCCTA

SEQ ID NO: 84
Amino acid sequence of light chain
variable region LC20
SYELTQPPSVSVAPGRTATLTC<u>GGDNIEHKSVH</u>WYQQKPGQAPLLIMY<u>YD</u>

<u>SDRPS</u>GVPERFSGSNFGNTATLTIDRVEAGDEADYYC<u>QVWDNFTEHPV</u>FG

RGTKLTVL

SEQ ID NO: 85
Nucleotide sequence of light chain
variable region LC21
TCCTATGAGCTGACACAGCCACCCTCAGTGTCAGTGGCCCCAGGCAGGAC

GGCCACACTTACCTGTGGGGGAGATAACATTGAACATAAAAGTGTGCACT

GGTACCAGCAGAAGCCAGGCCAGGCCCCTTTGTTGGTCATGTATTACGAT

AGTGACCGGCCATCAGGGGTCCCGGAGCGATTCTCTGGCTCCAACTCTGG

GAACACAGCCACTCTGACCATCACCAGGGTCGAAGCCGGGGATGAGGCCG

ACTATTATTGTCAAGTGTGGGATAATTTTACTGAACATCCGGTGTTCGGC

GGAGGGACCAAGCTGACCGTCCTA

SEQ ID NO: 86
Amino acid sequence of light chain
variable region LC21
SYELTQPPSVSVAPGRTATLTC<u>GGDNIEHKSVH</u>WYQQKPGQAPLLVMYY<u>D</u>

<u>SDRPS</u>GVPERFSGSNSGNTATLTITRVEAGDEADYYC<u>QVWDNFTEHPV</u>FG

GGTKLTVL

SEQ ID NO: 87
Nucleotide sequence of light chain
variable region LC22
CAGTCTGCCCTGACTCAGCCTGCCTCCGTGTCTGGGTCTCCTGGAGAGTC

GATCATCATCTCCTGCACTGGAACCAGCAGTGACGTTGGTGCTTATAACT

ATGTCTCCTGGTACCAACAGCACCTAGGCAAAGCCCCCAAACTCATGATT

TATGATGTCAGTCAGCGGCCCTCAGGGGTTTCTGATCGCTTCTCTGGCTC

CAAGTCTGGCAACACGGCCTCCCTGACAATCTCTGGGCTCCAGGCTGAGG

ACGAGGCCGATTATTATTGCAGCTCATTCACAGGTGACAGTGTTATATTC

GGCGGAGGGACCAAGCTGACCGTCCTA

SEQ ID NO: 88
Amino acid sequence of light chain
variable region LC22
QSALTQPASVSGSPGESIIISC<u>TGTSSDVGAYNYVS</u>WYQQHLGKAPKLMI Y<u>DVSQRPS</u>GVSDRFSGSKSGNTASLTISGLQAEDEADYYC<u>SSFTGDSVI</u>F

GGGTKLTVL

SEQ ID NO: 89
Nucleotide sequence of light chain
variable region LC23
CAGTCTGCCCTGACTCAGCCTCGCTCAGTGTCCGGGTCTCCTGGACAGTC

AGTCACCATTTCTTGTACTGGATCCCGCGGTGACGTTGGAGGTTATGACT

TTGTCTCCTGGTACCGTCAATACCCAGGCGAGGCCCCCCAACTCATTATT

TATGATGTCAGCGGGAGGCCATCAGGAGTCCCTGATCGCTTCTCTGGCTC

CAAGTCTGGCAACACGGCCTCCCTGACCATCTCTGGCTCCAGCCTGAAG

ATGAGGCTGATTATTATTGCTCTTCATACGCCGGCAGTGAGATTTATGTC

TTCGGAACTGGGACCAAGGTCACCGTCCTA

SEQ ID NO: 90
Amino acid sequence of light chain
variable region LC23
QSALTQPRSVSGSPGQSVTISC TGSRGDVGGYDFVS WYRQYPGEAPQLII

YDVSGRPS GVPDRFSGSKSGNTASLTISGLQPEDEADYYC SSYAGSEIYV

FGTGTKVTVL

SEQ ID NO: 91
Nucleotide sequence of light chain
variable region LC24
GATATTGTGATGACCCAGACTCCACTCTCCTCACATGTCACCCTTGGACA

GCCGGCCTCCATATCCTGCAGGTCTAGTCAGAGCCTCGTACGCAGTGATG

GCAACACGAACTTGAGTTGGCTTCACCAGAGGCCAGGCCAGCCTCCAAGA

CTCCTAATTTATACGATTTCTAACCGGTTCTCTGGGGTCCCAGACAGATT

CAGTGGCAGTGGGGCAGGGACAGATTTCACACTGAAAATCAGCAGGGTGG

AAGCTGAGGATGTCGGGGTTTATTACTGCATGCAAGCTACACAATATCCG

TACACTTTTGGCCAAGGGACCAAGGTGGAGATCAAACGT

SEQ ID NO: 92
Amino acid sequence of light chain
variable region LC24
DIVMTQTPLSSHVTLGQPASISC RSSQSLVRSDGNTNLS WLHQRPGQPPR

LLIY TISNRFS GVPDRFSGSGAGTDFTLKISRVEAEDVGVYYC MQATQYP

YTFGQGTKVEIKR

SEQ ID NO: 93
Nucleotide sequence of light chain
variable region LC25
GACATCCAGATGACCCAGTCTCCAGCCACCCTGTCTGTGTCTCCAGGGGA

AGGAGCCACCCTCTCCTGCAGGGCCAGTCAGAGTGTTACCAGCAACTTAG

CCTGGTACCAGCAGAAACCTGGCCAGGCTCCCAGGCTCCTCATCTATGAT

GCATCCAACAGGGCCGCTGGCATCCCAGACAGGTTCAGTGGCAGTGGGTC

TGGGACAGACTTCACTCTCACCATCAGCGGCCTAGAACCTGAAGATTTTG

CAGTTTATTACTGTCAGCAGCGTGACAGCTGGCCTCAAACTTTTGGCCAG

GGGACCAAGCTGGAGATCAAACGT

SEQ ID NO: 94
Amino acid sequence of light chain
variable region LC25
DIQMTQSPATLSVSPGEGATLSC RASQSVTSNLA WYQQKPGQAPRLLIY D

ASNRAAG IPDRFSGSGSGTDFTLTISGLEPEDFAVYYC QQRDSWPQT FGQ

GTKLEIKR

In the above amino acid sequences
of light and heavy chain variable
regions (SEQ ID NOs: 2, 4, 6, 8, 10,
12, 14, 16, 18, 20, 22, 24, 26, 28,
30, 32, 34, 36, 38, 40, 42, 44, 46,
48, 50, 52, 54, 56, 58, 60, 62, 64,
66, 68, 70, 72, 74, 76, 78, 80, 82,
84, 86, 88, 90, 92, and 94), the
underlined sequences, from left to
right, represent the CDR1, CDR2 and
CDR3, respectively.

The invention claimed is:

1. An isolated antibody selected from the group consisting of: (a) an antibody comprising the amino acid sequences as set forth in SEQ ID NO: 2 and SEQ ID NO: 46; (b) an antibody comprising the amino acid sequences as set forth in SEQ ID NO: 8 and SEQ ID NO: 52; (c) an antibody comprising the amino acid sequences as set forth in SEQ ID NO: 22 and SEQ ID NO: 64; (d) an antibody comprising the amino acid sequences as set forth in SEQ ID NO: 2 and SEQ ID NO: 48; (e) an antibody comprising the amino acid sequences as set forth in SEQ ID NO: 4 and SEQ ID NO: 48; (f) an antibody comprising the amino acid sequences a set forth in SEQ ID NO: 10 and SEQ ID NO: 54; (g) an antibody comprising the amino acid sequences as set forth in SEQ ID NO: 12 and SEQ ID NO: 56; (h) an antibody comprising the amino acid sequences as set forth in SEQ ID NO: 14 and SEQ ID NO: 58; (i) an antibody comprising the amino acid sequences as set forth in SEQ ID NO: 16 and SEQ ID NO: 60; (j) an antibody comprising the amino acid sequences as set forth in SEQ ID NO: 18 and SEQ ID NO: 62; (k) an antibody comprising the amino acid sequences as set forth in SEQ ID NO: 20 and SEQ ID NO: 64; (l) an antibody comprising the amino acid sequences as set forth in SEQ ID NO: 22 and SEQ ID NO: 66; (m) an antibody comprising the amino acid sequences as set forth in SEQ ID NO: 24 and SEQ ID NO: 68; (n) an antibody comprising the amino acid sequences as set forth in SEQ ID NO: 28 and SEQ ID NO: 72; (o) an antibody comprising the amino acid sequences as set forth in SEQ ID NO: 32 and SEQ ID NO: 76; (p) an antibody comprising the amino acid sequences as set forth in SEQ ID NO: 36 and SEQ ID NO: 80; (q) an antibody comprising the amino acid sequences as set forth in SEQ ID NO: 38 and SEQ ID NO: 82; (r) an antibody comprising the amino acid sequences as set forth in SEQ ID NO: 44 and SEQ ID NO: 88.

2. The isolated antibody according to claim 1, wherein the antibody is a monoclonal antibody.

3. The isolated antibody according to claim 1, wherein the antibody is selected from the group consisting of a human antibody, a humanized antibody, a single chain antibody, a diabody, a triabody, a tetrabody, a $F_{ab}$ fragment, a $F_{(ab')2}$ fragment, $F_d$, scF$_v$, a domain antibody, bispecific antibodies, a minibody, a scab, an IgD antibody, an IgE antibody, an IgM antibody, an IgG1 antibody, an IgG2 antibody, an Ig3 antibody, an IgG4 antibody, and artificial antibodies based upon protein scaffolds.

4. The isolated antibody according to claim 1, wherein the antibody is fused to other polypeptides or linked to other chemicals.

5. A pharmaceutical composition comprising the isolated antibody according to claim 1 and one or more pharmaceutically acceptable carrier.

6. An isolated nucleic acid comprising a polynucleotide sequence encoding the light chain variable domain and the heavy chain variable domain of the antibody according to claim 1.

7. The isolated nucleic acid according to claim 6, comprising one or more of the nucleotide sequences as set forth in SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, and 93.

8. A recombinant expression vector, comprising the nucleic acid according to claim 6.

9. A host cell transformed with the vector according to claim 8.

10. An isolated cell line, which produces the antibody according to claim 1, the heavy chain, light chain or an antigen-binding portion thereof.

11. A hybridoma producing the antibody according to claim 1, comprising the heavy chain, light chain or an antigen-binding portion thereof.

12. A method for treating patients with colon cancer, comprising the step of administering to the patient an effective amount of the pharmaceutical composition according to claim 5.

* * * * *